United States Patent
Li

(10) Patent No.: US 11,071,772 B2
(45) Date of Patent: *Jul. 27, 2021

(54) METHOD FOR PREVENTING AND TREATING TISSUE AND ORGAN FIBROSIS

(71) Applicant: Talengen International Limited, Hong Kong (CN)

(72) Inventor: Jinan Li, Guangdong (CN)

(73) Assignee: Talengen International Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/470,186

(22) PCT Filed: Jun. 19, 2017

(86) PCT No.: PCT/CN2017/089058
§ 371 (c)(1),
(2) Date: Jun. 14, 2019

(87) PCT Pub. No.: WO2018/107698
PCT Pub. Date: Jun. 21, 2018

(65) Prior Publication Data
US 2019/0365872 A1 Dec. 5, 2019

(30) Foreign Application Priority Data
Dec. 15, 2016 (WO) ................ PCT/CN2016/110174

(51) Int. Cl.
*A61K 38/48* (2006.01)
*A61P 17/02* (2006.01)
*A61P 9/10* (2006.01)
*A61P 3/06* (2006.01)
*A61P 11/00* (2006.01)
*A61P 1/16* (2006.01)
*A61P 19/04* (2006.01)
*A61K 45/06* (2006.01)

(52) U.S. Cl.
CPC .............. *A61K 38/484* (2013.01); *A61P 1/16* (2018.01); *A61P 3/06* (2018.01); *A61P 9/10* (2018.01); *A61P 11/00* (2018.01); *A61P 17/02* (2018.01); *A61P 19/04* (2018.01); *C12Y 304/21007* (2013.01); *A61K 45/06* (2013.01)

(58) Field of Classification Search
CPC ...... A61K 38/48; A61K 38/484; A61K 45/06; A61P 11/00; A61P 13/12; A61P 17/00; A61P 17/02; A61P 19/04; A61P 1/16; A61P 3/06; A61P 7/02; A61P 9/10; C12Y 304/21007; Y02A 50/402
See application file for complete search history.

(56) References Cited

U.S. PATENT DOCUMENTS

| 4,645,668 A | 2/1987 | Pinnell |
| 6,057,122 A | 5/2000 | Davidson |
| 7,067,492 B2 | 6/2006 | Ny |
| 10,441,639 B2 | 10/2019 | Blackman et al. |
| 2003/0054988 A1 | 3/2003 | Ji et al. |
| 2003/0147879 A1 | 8/2003 | Ny et al. |
| 2004/0043026 A1 | 3/2004 | Tuan et al. |
| 2004/0097455 A1 | 5/2004 | Borunda et al. |
| 2005/0124036 A1* | 6/2005 | Susilo ............... A61P 9/00 435/69.1 |
| 2005/0124534 A1 | 6/2005 | Noble et al. |
| 2005/0250694 A1* | 11/2005 | Ma ............... A61K 38/57 514/8.1 |
| 2015/0133458 A1 | 5/2015 | Mann |
| 2016/0362498 A1 | 12/2016 | Zhang et al. |
| 2018/0369345 A1 | 12/2018 | Li |
| 2019/0083586 A1 | 3/2019 | Li |
| 2019/0231854 A1 | 8/2019 | Robitaille |
| 2019/0307861 A1 | 10/2019 | Li |
| 2019/0314464 A1 | 10/2019 | Li |
| 2019/0314465 A1 | 10/2019 | Li |
| 2019/0314466 A1 | 10/2019 | Li |
| 2019/0314467 A1 | 10/2019 | Li |
| 2019/0314468 A1 | 10/2019 | Li |
| 2019/0328848 A1* | 10/2019 | Li ............... A61P 13/12 |
| 2019/0328849 A1 | 10/2019 | Li |
| 2019/0328850 A1* | 10/2019 | Li ............... A61P 3/10 |
| 2019/0343930 A1* | 11/2019 | Li ............... A61K 38/48 |
| 2019/0343931 A1* | 11/2019 | Li ............... A61K 38/48 |
| 2019/0351033 A1* | 11/2019 | Li ............... A61P 9/10 |
| 2020/0078449 A1* | 3/2020 | Li ............... A61K 38/484 |
| 2020/0085920 A1* | 3/2020 | Li ............... A61P 1/16 |
| 2020/0206324 A1* | 7/2020 | Li ............... A61K 38/48 |

FOREIGN PATENT DOCUMENTS

| CA | 2707266 A1 | 6/2009 |
| CA | 2823491 A1 | 7/2012 |
| CA | 2939897 A1 | 8/2015 |

(Continued)

OTHER PUBLICATIONS

International Search Report and Written Opinion dated Sep. 12, 2018, in connection with PCT/CN2018/091838.
Cerri et al., Management of idiopathic pulmonary fibrosis. Clin Chest Med. Mar. 2012;33(1):85-94. doi: 10.1016/j.ccm.2011.11. 005. Epub Dec. 28, 2011. Review.
Faller et al., Inhaled hydrogen sulfide protects against lipopolysaccharide-induced acute lung injury in mice. Med Gas Res. Oct. 1, 2012;2(1):26. doi: 10.1186/2045-9912-2-26.
Gomez-Arroyo et al., The monocrotaline model of pulmonary hypertension in perspective. Am J Physiol Lung Cell Mol Physiol. Feb. 15, 2012;302(4):L363-9. doi: 10.1152/ajplung.00212.2011. Epub Sep. 30, 2011. Review.

(Continued)

*Primary Examiner* — Marcela M Cordero Garcia
(74) *Attorney, Agent, or Firm* — Wolf, Greenfield & Sacks, P.C.

(57) ABSTRACT

The present invention relates to a method for preventing and treating tissue and organ fibrosis, comprising administering an effective amount of plasminogen to a subject.

29 Claims, 7 Drawing Sheets

Specification includes a Sequence Listing.

(56) References Cited

FOREIGN PATENT DOCUMENTS

| | | | |
|---|---|---|---|
| CN | 1585649 A | 2/2005 | |
| CN | 1668312 A | 9/2005 | |
| CN | 1723197 A | 1/2006 | |
| CN | 1768138 A | 5/2006 | |
| CN | 101044136 A | 9/2007 | |
| CN | 101573134 A | 11/2009 | |
| CN | 101628113 A | 1/2010 | |
| CN | 101918548 A | 12/2010 | |
| CN | 102121023 A | 7/2011 | |
| CN | 102482338 A | 5/2012 | |
| CN | 103384722 A | 11/2013 | |
| CN | 104914247 A | 9/2015 | |
| CN | 105705520 A | 6/2016 | |
| CN | 106029884 A | 10/2016 | |
| CN | 106890318 A | 6/2017 | |
| CN | 106890320 A | 6/2017 | |
| CN | 106890324 A | 6/2017 | |
| DE | 00980071 T1 | 3/2005 | |
| DK | 1411128 T3 | 2/2009 | |
| EP | 0307847 B1 | 12/1992 | |
| EP | 1411128 A1 | 4/2004 | |
| KR | 101467109 B1 | 12/2014 | |
| TW | 201625294 A | 7/2016 | |
| TW | I568745 B | 2/2017 | |
| TW | 201722465 A | 7/2017 | |
| TW | I624268 B | 5/2018 | |
| TW | 201822783 A | 7/2018 | |
| TW | 201822795 A | 7/2018 | |
| TW | 201822807 A | 7/2018 | |
| TW | 201822808 A | 7/2018 | |
| TW | I642442 B | 12/2018 | |
| TW | I669130 B | 8/2019 | |
| WO | WO 99/00420 A1 | 1/1999 | |
| WO | WO 00/10506 A2 | 3/2000 | |
| WO | WO 02/44393 A1 | 6/2002 | |
| WO | WO 2004/041155 A2 | 5/2004 | |
| WO | WO 2004/052853 A2 | 6/2004 | |
| WO | WO 2006/023864 A1 | 3/2006 | |
| WO | WO 2008/026999 A2 | 3/2008 | |
| WO | WO 2010/111271 A1 | 9/2010 | |
| WO | WO 2011/004011 A1 | 1/2011 | |
| WO | WO 2011/057138 A1 | 5/2011 | |
| WO | WO 2011/139973 A2 | 11/2011 | |
| WO | WO 2015/023752 A1 | 2/2015 | |
| WO | WO 2015/026494 A2 | 2/2015 | |

OTHER PUBLICATIONS

Li et al., Glucocorticoid with cyclophosphamide for paraquat-induced lung fibrosis. Cochrane Database Syst Rev. Aug. 7, 2014;(8):CD008084. doi: 10.1002/14651858.CD008084.pub4. Review.
Liu et al., Radix puerariae extracts ameliorate paraquat-induced pulmonary fibrosis by attenuating follistatin-like 1 and nuclear factor erythroid 2p45-related factor-2 signalling pathways through downregulation of miRNA-21 expression. BMC Complement Altern Med. Jan. 12, 2016;16:11. doi: 10.1186/s12906-016-0991-6.
Scott et al., Extracellular matrix, supramolecular organisation and shape. J Anat. Oct. 1995;187 ( Pt 2):259-69. Review.
Specks et al., Increased expression of type VI collagen in lung fibrosis. Am J Respir Crit Care Med. Jun. 1995;151(6):1956-64.
Farkas et al., Pulmonary hypertension and idiopathic pulmonary fibrosis: a tale of angiogenesis, apoptosis, and growth factors. Am J Respir Cell Mol Biol. Jul. 2011;45(1):1-15. doi: 10.1165/rcmb.2010-0365TR. Epub Nov. 5, 2010. Review.
Jin et al., Combination of human plasminogen kringle 5 with ionizing radiation significantly enhances the efficacy of antitumor effect. Int J Cancer. Dec. 1, 2007;121(11):2539-46.
[No Author Listed] Treatment Options. Pulmonary Fibrosis Foundation. 2019. https://www.pulmonaryfibrosis.org/life-with-pt/pulmonary-fibrosis-treatment-options [last accessed Nov. 7, 2019], 14 pages.

International Search Report and Written Opinion dated Sep. 18, 2017, in connection with PCT/CN2014/089053.
International Search Report and Written Opinion dated Sep. 11, 2017, in connection with PCT/CN2014/089054.
International Search Report and Written Opinion dated Sep. 14, 2017, in connection with PCT/CN2014/089055.
International Search Report and Written Opinion dated Aug. 23, 2017, in connection with PCT/CN2014/089056.
International Search Report and Written Opinion dated Aug. 30, 2017, in connection with PCT/CN2014/089057.
International Search Report and Written Opinion dated Aug. 24, 2017, in connection with PCT/CN2014/089058.
Beier et al., Alcoholic liver disease and the potential role of plasminogen activator inhibitor-1 and fibrin metabolism. Exp. Biol. Med. (Maywood). Jan. 31, 2012;237(1):1-9.
Edgtton et al., Plasmin is not protective in experimental renal interstitial fibrosis. Kidney Intl. Jul. 2004;66(1):68-76.
Eitzman et al., Bleomycin-induced pulmonary fibrosis in transgenic mice that either lack or overexpress the murine plasminogen activator inhibitor-1 gene. J. Clin. Invest. Jan. 1996;97(1):232-7.
Fisher et al., Displacement of tissue bound plasminogen by glucose: a possible mechanism in the pathogenesis of diabetic nephropathy. Endocrinol Metab. Nov. 30, 1997;4:371-6.
Genbank Submission; NIH/NCBI, Accession No. NP-000292.1, Plasminogen isoform 1 precursor [*Homo sapiens*]. May 4, 2019, 4 pages.
Ghosh et al., PAI-1 in tissue fibrosis. J Cell Physiol. Feb. 2012;227(2):493-507.
Giorgio-Miller et al., Fibrin-induced skin fibrosis in mice deficient in tissue plasminogen activator. Am J Pathol. Sep. 30, 2005;167(3):721-32.
Hattori et al., Bleomycin-induced pulmonary fibrosis in fibrinogen-null mice. J Clin Invest. 2000;106(11):1341-50.
He et al., Systemic Scleroderma and Tissue Fibrosis. J Clin Dermatol. Aug. 31, 2009;38(8):546-8.
Hu et al., Novel actions of tissue-type plasminogen activator in chronic kidney disease: a paradigm shift. Front Biosci. May 2008;13:5174-86.
Kitching et al., Plasminogen and plasminogen activators protect against renal injury in crescentic glomerulonephritis. J Exp Med. Mar. 3, 1997;185(5):963-8.
Li et al., Efficacy observation of integrated therapy of Urokinase and interferon for fibrosis in aged tumour patients after radiotherapy. Chin J Oncol Prev Treat. Jun. 2016;8(3):179-80.
Liu et al., Plasminogen: structure, function and evolution. J Ocean Univ China. Oct. 2010;40(10):69-74.
Lugea et al., Pancreas recovery following caerulein-induced pancreatitis is impaired in plasminogen deficient mice. Gastroenterology. Sep. 2006;131(3):885-899.
Marudamuthu et al., Plasminogen activator inhibitor-1 suppresses profibrotic responses in fibroblasts from fibrotic lungs. J Biol Chem. Apr. 10, 2015;290(15):9428-41.
Pohl et al., Plasminogen deficiency leads to impaired lobular reorganization and matrix accumulation after chronic liver injury. Am J Pathol. Dec. 2001;159(6):2179-86.
Pohl et al., Plasminogen deficiency accelerates the development of hepatic fibrosis in mice. Gastroenterology. Apr. 2000;118(4):A989. Paragraph 1129.
Puccetti et al., Dyslipidemias and fibrinolysis. Ital Heart J. Oct. 2002;3(10):579-86.
Schott et al., Therapy with a purified plasminogen concentrate in an infant with ligneous conjunctivitis and homozygous plasminogen deficiency. N Engl J Med. Dec. 1998;339(23):1679-86.
Swaisgood et al., The development of bleomycin induced pulmonary fibrosis in mice deficient for components of the fibrinolytic system. Am J Pathol. Jul. 2000;157(1):177-87.
Wilson et al., The safety and efficacy of low-dose tissue plasminogen activator in the treatment of systemic sclerosis. J Dermatol. Sep. 1995;22(9):637-42.
Wu et al., Experience of using Urokinase to treat systemic sclerosis. Foreign Medical Sciences Section of Dermatology and Venereology. Br J Dermatol. May 1982;104:105.

(56) References Cited

OTHER PUBLICATIONS

Xiao et al., Plasminogen deficiency accelerates vessel wall disease in mice predisposed to atherosclerosis. Proc Natl Acad Sci. Sep. 1997;94:10335-40.

Yang et al., Disruption of tissue-type plasminogen activator gene in mice reduces renal interstitial fibrosis in obstructive nephropathy. J Clin Invest. Dec. 2002;110(10):1525-38.

Yang et al., Pathological mechanisms of oral submucous fibrosis. Institute Biochem Biotech. Chung Shan Medical University. Jun. 2005. Doctor Thesis. pp. 1-136.

Zhu et al., The role of the plasminogen activator inhibitor-1 in the pathogenesis of hepatic fibrosis, medicine & public health. Chinese Selected Doctoral Dissertations and Master's Theses Full-Text Databases. Apr. 15, 2007;E064-4:64-7.

Zhu et al., Expression and significance of plasminogen activator inhibitor-1 in hepatic fibrosis. Chinese Hepatol. Apr. 2006;11(2):3 pages.

[No Author Listed] Score_Search_Results_16470173_7_pages.

[No Author Listed] Uniprot Protein Database. Accession No. P00747, Human PLMN. Accessed Aug. 10, 2020; 14 pages.

Aisina et al., Structure and functions of plasminogen/plasmin system. Bioorg Khim. Nov.-Dec. 2014;40(6):642-57. Russian. doi: 10.1134/s1068162014060028.

Badylak et al., The beneficial effect of lys-plasminogen upon the thrombolytic efficacy of urokinase in a dog model of peripheral arterial thrombosis. Haemostasis. 1991;21(5):278-85. doi: 10.1159/000216237.

Bergheim et al. Metformin prevents alcohol-induced liver injury in the mouse: Critical role of plasminogen activator inhibitor-1. Gastroenterology. Jun. 2006;130(7):2099-112. doi: 10.1053/j.gastro.2006.03.020.

Gutierrez et al., Tumor development is retarded in mice lacking the gene for urokinase-type plasminogen activator or its inhibitor, plasminogen activator inhibitor-1. Cancer Res. Oct. 15, 2000;60(20):5839-47.

Haraguchi et al., t-PA promotes glomerular plasmin generation and matrix degradation in experimental glomerulonephritis. Kidney Int. Jun. 2001;59(6):2146-55. doi: 10.1046/j.1523-1755.2001.00729.x.

Kanduc et al., Homology, similarity, and identity in peptide epitope immunodefinition. J Pept Sci. Aug. 2012;18(8):487-94. doi: 10.1002/psc.2419. Epub Jun. 14, 2012.

Lijnen, Pathophysiology of the plasminogen/plasmin system. Int J Clin Lab Res. 1996;26(1):1-6. doi: 10.1007/BF02644767.

Matsuoka et al., Plasminogen-mediated activation and release of hepatocyte growth factor from extracellular matrix. Am J Respir Cell Mol Biol. Dec. 2006;35(6):705-13. doi: 10.1165/rcmb.2006-0006OC. Epub Jul. 13, 2006.

O'Reilly et al., Angiostatin: a circulating endothelial cell inhibitor that suppresses angiogenesis and tumor growth. Cold Spring Harb Symp Quant Biol. 1994;59:471-82. doi: 10.1101/sqb.1994.059.01.052.

Oh et al., The role of plasminogen in angiogenesis in vivo. J Thromb Haemost. Aug. 2003;1(8):1683-7. doi: 10.1046/j.1538-7836.2003.00182.x.

Stefansson et al., Inhibition of angiogenesis in vivo by plasminogen activator inhibitor-1. J Biol Chem. Mar. 16, 2001;276(11):8135-41. doi: 10.1074/jbc.M007609200. Epub Nov. 16, 2000.

Takeshita et al., Increased expression of plasminogen activator inhibitor-1 in cardiomyocytes contributes to cardiac fibrosis after myocardial infarction. Am J Pathol. Feb. 2004;164(2):449-56. doi: 10.1016/S0002-9440(10)63135-5.

Thacil et al., Ligneous conjunctivitis with plasminogen deficiency. Br J Haematol. May 2009;145(3):269. doi: 10.1111/j.1365-2141.2008.07445.x.

Vogten et al., Angiostatin inhibits experimental liver fibrosis in mice. Int J Colorectal Dis. Jul. 2004;19(4):387-94. doi: 10.1007/s00384-003-0562-4. Epub Jan. 10, 2004.

* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural
      plasminogen(Glu-PLG,Glu-plasminogen)without the signal peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
```

```
aatggcatca cctgtcaaaa atggagttcc acttctcccc acagacctag attctcacct    360
gctacacacc cctcagaggg actggaggag aactactgca ggaatccaga caacgatccg    420
caggggccct ggtgctatac tactgatcca gaaagagat atgactactg cgacattctt     480
gagtgtgaag aggaatgtat gcattgcagt ggagaaaact atgacggcaa aatttccaag    540
accatgtctg gactggaatg ccaggcctgg gactctcaga gcccacacgc tcatggatac    600
attccttcca aatttccaaa caagaacctg aagaagaatt actgtcgtaa ccccgatagg    660
gagctgcggc cttggtgttt caccaccgac cccaacaagc gctgggaact tgtgacatc     720
ccccgctgca caacctcc accatcttct ggtcccacct accagtgtct gaagggaaca     780
ggtgaaaact atcgcgggaa tgtggctgtt accgtgtccg gcacacctg tcagcactgg     840
agtgcacaga cccctcacac acataacagg acaccagaaa acttcccctg caaaaatttg    900
gatgaaaact actgccgcaa tcctgacgga aaaagggccc catggtgcca tacaaccaac    960
agccaagtgc ggtgggagta ctgtaagata ccgtcctgtg actcctcccc agtatccacg   1020
gaacaattgg ctcccacagc accacctgag ctaacccctg tggtccagga ctgctaccat   1080
ggtgatggac agagctaccg aggcacatcc tccaccacca ccacaggaaa gaagtgtcag   1140
tcttggtcat ctatgacacc acaccggcac cagaagaccc cagaaaacta cccaaatgct   1200
ggcctgacaa tgaactactg caggaatcca gatgccgata aaggcccctg gtgttttacc   1260
acagacccca gcgtcaggtg ggagtactgc aacctgaaaa aatgctcagg aacagaagcg   1320
agtgttgtag cacctccgcc tgttgtcctg cttccagatg tagagactcc ttccgaagaa   1380
gactgtatgt ttgggaatgg gaaaggatac cgaggcaaga gggcgaccac tgttactggg   1440
acgccatgcc aggactgggc tgcccaggag ccccatagac acagcatttt cactccagag   1500
acaaatccac gggcgggtct ggaaaaaaat tactgccgta accctgatgg tgatgtaggt   1560
ggtccctggt gctacacgac aaatccaaga aaactttacg actactgtga tgtccctcag   1620
tgtgcggccc cttcatttga ttgtgggaag cctcaagtgg agccgaagaa atgtcctgga   1680
agggttgtag gggggtgtgt ggcccaccca cattcctggc cctggcaagt cagtcttaga   1740
acaaggtttg aatgcactt ctgtggaggc accttgatat ccccagagtg ggtgttgact    1800
gctgcccact gcttggagaa gtccccaagg ccttcatcct acaaggtcat cctgggtgca   1860
caccaagaag tgaatctcga accgcatgtt caggaaatag aagtgtctag gctgttcttg   1920
gagcccacac gaaaagatat tgccttgcta aagctaagca gtcctgccgt catcactgac   1980
aaagtaatcc cagcttgtct gccatcccca aattatgtgg tcgctgaccg gaccgaatgt   2040
ttcatcactg gctggggaga aacccaaggt actttggag ctggccttct caaggaagcc    2100
cagctccctg tgattgagaa taagtgtgc aatcgctatg agtttctgaa tggaagagtc    2160
caatccaccg aactctgtgc tgggcatttg gccggaggca ctgacagttg ccagggtgac   2220
agtggaggtc ctctggtttg cttcgagaag gacaaataca ttttacaagg agtcacttct   2280
tggggtcttg gctgtgcacg ccccaataag cctggtgtct atgttcgtgt ttcaaggttt   2340
gttacttgga ttgagggagt gatgagaaat aattaa                            2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
            50                  55                  60

Ile Ile Ile Arg Met Arg Asp Val Val Leu Phe Glu Lys Lys Val Tyr
65              70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
                100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
            195                 200                 205

Asn Leu Lys Lys Asn Tyr Cys Arg Asn Pro Asp Arg Glu Leu Arg Pro
210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
            290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
            370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro

```
                    405                 410                 415
Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
            450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
                500                 505                 510

Arg Asn Pro Asp Gly Asp Val Gly Gly Pro Trp Cys Tyr Thr Thr Asn
                515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
                580                 585                 590

Ile Ser Pro Glu Trp Val Leu Thr Ala Ala His Cys Leu Glu Lys Ser
                595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
                675                 680                 685

Gln Gly Thr Phe Gly Ala Gly Leu Leu Lys Glu Ala Gln Leu Pro Val
            690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
            755                 760                 765

Asn Lys Pro Gly Val Tyr Val Arg Val Ser Arg Phe Val Thr Trp Ile
            770                 775                 780

Glu Gly Val Met Arg Asn Asn
785                 790

<210> SEQ ID NO 3
<211> LENGTH: 2433
<212> TYPE: DNA
<213> ORGANISM: Artificial sequence
```

<220> FEATURE:
<223> OTHER INFORMATION: nucleotide sequence coding for the natural
plasminogen(from swiss prot)with the signal peptide

<400> SEQUENCE: 3

| | | | | | |
|---|---|---|---|---|---|
| atggaacata | aggaagtggt | tcttctactt | cttttatttc | tgaaatcagg | tcaaggagag | 60 |
| cctctggatg | actatgtgaa | tacccagggg | gcttcactgt | tcagtgtcac | taagaagcag | 120 |
| ctgggagcag | gaagtataga | agaatgtgca | gcaaaatgtg | aggaggacga | agaattcacc | 180 |
| tgcagggcat | tccaatatca | cagtaaagag | caacaatgtg | tgataatggc | tgaaaacagg | 240 |
| aagtcctcca | taatcattag | gatgagagat | gtagttttat | ttgaaaagaa | agtgtatctc | 300 |
| tcagagtgca | agactgggaa | tggaaagaac | tacagaggga | cgatgtccaa | aacaaaaaat | 360 |
| ggcatcacct | gtcaaaaatg | gagttccact | tctcccccaca | gacctagatt | ctcacctgct | 420 |
| acacacccct | cagagggact | ggaggagaac | tactgcagga | atccagacaa | cgatccgcag | 480 |
| gggcctgggt | gctatactac | tgatccagaa | aagagatatg | actactgcga | cattcttgag | 540 |
| tgtgaagagg | aatgtatgca | ttgcagtgga | gaaaactatg | acggcaaaat | ttccaagacc | 600 |
| atgtctggac | tggaatgcca | ggcctgggac | tctcagagcc | cacacgctca | tggatacatt | 660 |
| ccttccaaat | ttccaaacaa | gaacctgaag | aagaattact | gtcgtaaccc | cgataggga | 720 |
| ctgcggcctt | ggtgtttcac | caccgacccc | aacaagcgct | gggaactttg | tgacatcccc | 780 |
| cgctgcacaa | cacctccacc | atcttctggt | cccacctacc | agtgtctgaa | gggaacaggt | 840 |
| gaaaactatc | gcgggaatgt | ggctgttacc | gtgtccgggc | acacctgtca | gcactggagt | 900 |
| gcacagaccc | ctcacacaca | taacaggaca | ccagaaaact | tccctgcaa | aaatttggat | 960 |
| gaaaactact | gccgcaatcc | tgacggaaaa | agggccccat | ggtgccatac | aaccaacagc | 1020 |
| caagtgcggt | gggagtactg | taagataccg | tcctgtgact | cctccccagt | atccacggaa | 1080 |
| caattggctc | ccacagcacc | acctgagcta | acccctgtgg | tccaggactg | ctaccatggt | 1140 |
| gatggacaga | gctaccgagg | cacatcctcc | accaccacca | caggaaagaa | gtgtcagtct | 1200 |
| tggtcatcta | tgacaccaca | ccggcaccag | aagaccccag | aaaactaccc | aaatgctggc | 1260 |
| ctgacaatga | actactgcag | gaatccagat | gccgataaag | gccccctggtg | ttttaccaca | 1320 |
| gaccccagcg | tcaggtggga | gtactgcaac | ctgaaaaat | gctcaggaac | agaagcgagt | 1380 |
| gttgtagcac | ctccgcctgt | tgtcctgctt | ccagatgtag | agactccttc | gaagaagac | 1440 |
| tgtatgtttg | ggaatgggaa | aggataccga | ggcaagaggg | cgaccactgt | tactgggacg | 1500 |
| ccatgccagg | actgggctgc | ccaggagccc | catagacaca | gcattttcac | tccagacaca | 1560 |
| aatccacggg | cgggtctgga | aaaaaattac | tgccgtaacc | ctgatggtga | tgtaggtggt | 1620 |
| ccctggtgct | acacgacaaa | tccaagaaaa | ctttacgact | actgtgatgt | ccctcagtgt | 1680 |
| gcggcccctt | catttgattg | tgggaagcct | caagtggagc | gaagaaatg | tcctggaagg | 1740 |
| gttgtagggg | ggtgtgtggc | ccacccacat | tcctggccct | ggcaagtcag | tcttagaaca | 1800 |
| aggtttggaa | tgcacttctg | tggaggcacc | ttgatatccc | cagagtgggt | gttgactgct | 1860 |
| gcccactgct | tggagaagtc | cccaaggcct | tcatcctaca | aggtcatcct | gggtgcacac | 1920 |
| caagaagtga | atctcgaacc | gcatgttcag | gaaatagaag | tgtctaggct | gttcttggag | 1980 |
| cccacacgaa | aagatattgc | cttgctaaag | ctaagcagtc | ctgccgtcat | cactgacaaa | 2040 |
| gtaatcccag | cttgtctgcc | atccccaaat | tatgtggtcg | ctgaccggac | cgaatgtttc | 2100 |
| atcactggct | ggggagaaac | ccaaggtact | tttggagctg | ccttctcaa | ggaagcccag | 2160 |
| ctccctgtga | ttgagaataa | agtgtgcaat | cgctatgagt | ttctgaatgg | aagagtccaa | 2220 |

```
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                 2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen(from swiss prot)with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320
```

```
Glu Asn Tyr Cys Arg Asn Pro Asp Gly Lys Arg Ala Pro Trp Cys His
            325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
            355                 360                 365

Glu Leu Thr Pro Val Val Gln Asp Cys Tyr His Gly Asp Gly Gln Ser
            370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
            405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
            450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
            485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
            515                 520                 525

Asn Tyr Cys Arg Asn Pro Asp Gly Asp Val Gly Gly Pro Trp Cys Tyr
            530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
            565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
            595                 600                 605

Gly Thr Leu Ile Ser Pro Glu Trp Val Leu Thr Ala Ala His Cys Leu
            610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
            645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
            690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
            725                 730                 735
```

```
Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for
      LYS77-PLG(Lys-plasminogen)

<400> SEQUENCE: 5
```

| | | | | |
|---|---|---|---|---|
| aaagtgtatc | tctcagagtg | caagactggg | aatggaaaga | actacagagg gacgatgtcc | 60 |
| aaaacaaaaa | atggcatcac | ctgtcaaaaa | tggagttcca | cttctcccca cagacctaga | 120 |
| ttctcacctg | ctacacaccc | ctcagaggga | ctggaggaga | actactgcag gaatccagac | 180 |
| aacgatccgc | aggggccctg | tgctatact | actgatccag | aaaagagata tgactactgc | 240 |
| gacattcttg | agtgtgaaga | ggaatgtatg | cattgcagtg | gagaaaacta tgacggcaaa | 300 |
| atttccaaga | ccatgtctgg | actggaatgc | caggcctggg | actctcagag cccacacgct | 360 |
| catggataca | ttccttccaa | atttccaaac | aagaacctga | agaagaatta ctgtcgtaac | 420 |
| cccgataggg | agctgcggcc | ttggtgtttc | accaccgacc | caacaagcg ctgggaactt | 480 |
| tgtgacatcc | cccgctgcac | aacacctcca | ccatcttctg | gtcccaccta ccagtgtctg | 540 |
| aagggaacag | gtgaaaacta | tcgcgggaat | gtggctgtta | ccgtgtccgg gcacacctgt | 600 |
| cagcactgga | gtgcacagac | ccctcacaca | cataacagga | caccagaaaa cttcccctgc | 660 |
| aaaaatttgg | atgaaaacta | ctgccgcaat | cctgacggaa | aaagggcccc atggtgccat | 720 |
| acaaccaaca | gccaagtgcg | gtgggagtac | tgtaagatac | cgtcctgtga ctcctcccca | 780 |
| gtatccacgg | aacaattggc | tcccacagca | ccacctgagc | taacccctgt ggtccaggac | 840 |
| tgctaccatg | gtgatggaca | gagctaccga | ggcacatcct | ccaccaccac cacaggaaag | 900 |
| aagtgtcagt | cttggtcatc | tatgacacca | caccggcacc | agaagacccc agaaaactac | 960 |
| ccaaatgctg | gcctgacaat | gaactactgc | aggaatccag | atgccgataa aggcccctgg | 1020 |
| tgttttacca | cagaccccag | cgtcaggtgg | gagtactgca | acctgaaaaa atgctcagga | 1080 |
| acagaagcga | gtgttgtagc | acctccgcct | gttgtcctgc | ttccagatgt agagactcct | 1140 |
| tccgaagaag | actgtatgtt | tgggaatggg | aaaggatacc | gaggcaagag ggcgaccact | 1200 |
| gttactggga | cgccatgcca | ggactgggct | gcccaggagc | ccatagaca cagcattttc | 1260 |
| actccagaga | caaatccacg | ggcgggtctg | gaaaaaaatt | actgccgtaa ccctgatggt | 1320 |
| gatgtaggtg | gtccctggtg | ctacacgaca | aatccaagaa | aactttacga ctactgtgat | 1380 |
| gtccctcagt | gtgcggcccc | ttcatttgat | tgtgggaagc | tcaagtggga gccgaagaaa | 1440 |
| tgtcctggaa | gggttgtagg | ggggtgtgtg | gcccacccac | attcctggcc ctggcaagtc | 1500 |
| agtcttagaa | caaggtttgg | aatgcacttc | tgtggaggca | ccttgatatc cccagagtgg | 1560 |
| gtgttgactg | ctgcccactg | cttggagaag | tccccaaggc | cttcatccta caaggtcatc | 1620 |

```
ctgggtgcac accaagaagt gaatctcgaa ccgcatgttc aggaaataga agtgtctagg   1680
ctgttcttgg agcccacacg aaaagatatt gccttgctaa agctaagcag tcctgccgtc   1740
atcactgaca agtaatccc  agcttgtctg ccatccccaa attatgtggt cgctgaccgg   1800
accgaatgtt tcatcactgg ctggggagaa acccaaggta cttttggagc tggccttctc   1860
aaggaagccc agctccctgt gattgagaat aaagtgtgca atcgctatga gtttctgaat   1920
ggaagagtcc aatccaccga actctgtgct gggcatttgg ccggaggcac tgacagttgc   1980
cagggtgaca gtggaggtcc tctggtttgc ttcgagaagg acaaatacat tttacaagga   2040
gtcacttctt ggggtcttgg ctgtgcacgc cccaataagc ctggtgtcta tgttcgtgtt   2100
tcaaggtttg ttacttggat tgagggagtg atgagaaata attaa                   2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of
      LYS77-PLG(Lys-plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
```

-continued

```
                260                 265                 270
Glu Leu Thr Pro Val Gln Asp Cys Tyr His Gly Asp Gly Gln Ser
            275                 280                 285
Tyr Arg Gly Thr Ser Thr Thr Thr Gly Lys Lys Cys Gln Ser
            290                 295                 300
Trp Ser Ser Met Thr Pro His Arg His Gln Lys Thr Pro Glu Asn Tyr
305                 310                 315                 320
Pro Asn Ala Gly Leu Thr Met Asn Tyr Cys Arg Asn Pro Asp Ala Asp
                325                 330                 335
Lys Gly Pro Trp Cys Phe Thr Thr Asp Pro Ser Val Arg Trp Glu Tyr
            340                 345                 350
Cys Asn Leu Lys Lys Cys Ser Gly Thr Glu Ala Ser Val Val Ala Pro
            355                 360                 365
Pro Pro Val Val Leu Leu Pro Asp Val Glu Thr Pro Ser Glu Glu Asp
370                 375                 380
Cys Met Phe Gly Asn Gly Lys Gly Tyr Arg Gly Lys Arg Ala Thr Thr
385                 390                 395                 400
Val Thr Gly Thr Pro Cys Gln Asp Trp Ala Ala Gln Glu Pro His Arg
                405                 410                 415
His Ser Ile Phe Thr Pro Glu Thr Asn Pro Arg Ala Gly Leu Glu Lys
                420                 425                 430
Asn Tyr Cys Arg Asn Pro Asp Gly Asp Val Gly Gly Pro Trp Cys Tyr
                435                 440                 445
Thr Thr Asn Pro Arg Lys Leu Tyr Asp Tyr Cys Asp Val Pro Gln Cys
            450                 455                 460
Ala Ala Pro Ser Phe Asp Cys Gly Lys Pro Gln Val Glu Pro Lys Lys
465                 470                 475                 480
Cys Pro Gly Arg Val Val Gly Gly Cys Val Ala His Pro His Ser Trp
                485                 490                 495
Pro Trp Gln Val Ser Leu Arg Thr Arg Phe Gly Met His Phe Cys Gly
            500                 505                 510
Gly Thr Leu Ile Ser Pro Glu Trp Val Leu Thr Ala Ala His Cys Leu
            515                 520                 525
Glu Lys Ser Pro Arg Pro Ser Ser Tyr Lys Val Ile Leu Gly Ala His
            530                 535                 540
Gln Glu Val Asn Leu Glu Pro His Val Gln Glu Ile Glu Val Ser Arg
545                 550                 555                 560
Leu Phe Leu Glu Pro Thr Arg Lys Asp Ile Ala Leu Leu Lys Leu Ser
                565                 570                 575
Ser Pro Ala Val Ile Thr Asp Lys Val Ile Pro Ala Cys Leu Pro Ser
                580                 585                 590
Pro Asn Tyr Val Val Ala Asp Arg Thr Glu Cys Phe Ile Thr Gly Trp
            595                 600                 605
Gly Glu Thr Gln Gly Thr Phe Gly Ala Gly Leu Leu Lys Glu Ala Gln
            610                 615                 620
Leu Pro Val Ile Glu Asn Lys Val Cys Asn Arg Tyr Glu Phe Leu Asn
625                 630                 635                 640
Gly Arg Val Gln Ser Thr Glu Leu Cys Ala Gly His Leu Ala Gly Gly
                645                 650                 655
Thr Asp Ser Cys Gln Gly Asp Ser Gly Gly Pro Leu Val Cys Phe Glu
                660                 665                 670
Lys Asp Lys Tyr Ile Leu Gln Gly Val Thr Ser Trp Gly Leu Gly Cys
                675                 680                 685
```

Ala Arg Pro Asn Lys Pro Gly Val Tyr Val Arg Val Ser Arg Phe Val
    690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for
      delta-plg(delta-plasminogen)

<400> SEQUENCE: 7

```
gagcctctgg atgactatgt aataccag ggggcttcac tgttcagtgt cactaagaag      60
cagctgggag caggaagtat agaagaatgt gcagcaaaat gtgaggagga cgaagaattc    120
acctgcaggg cattccaata tcacagtaaa gagcaacaat gtgtgataat ggctgaaaac    180
aggaagtcct ccataatcat taggatgaga gatgtagttt tatttgaaaa gaaagtgtat    240
ctctcagagt gcaagactgg gaatggaaag aactacagag gacgatgtc caaaacaaaa    300
aatggcatca cctgtcaaaa atggagttcc acttctcccc acagacctag attctcacct    360
gctacacacc cctcagaggg actggaggag aactactgca ggaatccaga caacgatccg    420
caggggccct ggtgctatac tactgatcca gaaaagagat atgactactg cgacattctt    480
gagtgtgaag aggcggcccc ttcatttgat tgtgggaagc ctcaagtgga gccgaagaaa    540
tgtcctggaa gggttgtagg ggggtgtgtg gcccacccac attcctggcc ctggcaagtc    600
agtcttagaa caaggtttgg aatgcacttc tgtggaggca ccttgatatc cccagagtgg    660
gtgttgactg ctgcccactg cttggagaag tccccaaggc cttcatccta caaggtcatc    720
ctgggtgcac accaagaagt gaatctcgaa ccgcatgttc aggaaataga agtgtctagg    780
ctgttcttgg agcccacacg aaaagatatt gccttgctaa agctaagcag tcctgccgtc    840
atcactgaca agtaatccc agcttgtctg ccatccccaa attatgtggt cgctgaccgg    900
accgaatgtt tcatcactgg ctggggagaa acccaaggta cttttggagc tggccttctc    960
aaggaagccc agctccctgt gattgagaat aaagtgtgca atcgctatga gtttctgaat    1020
ggaagagtcc aatccaccga actctgtgct gggcatttgg ccggaggcac tgacagttgc    1080
cagggtgaca gtggaggtcc tctggttgc ttcgagaagg acaaatacat tttacaagga    1140
gtcacttctt ggggtcttgg ctgtgcacgc cccaataagc ctggtgtcta tgttcgtgtt    1200
tcaaggtttg ttacttggat tgagggagtg atgagaaata attaa                   1245
```

<210> SEQ ID NO 8
<211> LENGTH: 414
<212> TYPE: PRT
<213> ORGANISM: Artificial sequence
<220> FEATURE:
<223> OTHER INFORMATION: amino acid sequence of
      delta-plg(delta-plasminogen)

<400> SEQUENCE: 8

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

```
Ser Lys Glu Gln Gln Cys Val Ile Met Ala Glu Asn Arg Lys Ser Ser
     50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                 85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410
```

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for
      Mini-plg(mini-plasminogen)

<400> SEQUENCE: 9

```
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aaggataccg aggcaagagg gcgaccactg ttactgggac gccatgccag     180
gactgggctg cccaggagcc ccatagacac agcattttca ctccagagac aaatccacgg     240
gcgggtctgg aaaaaaatta ctgccgtaac cctgatggtg atgtaggtgg tccctggtgc     300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt ccccaaggcc ttcatcctac aaggtcatcc tgggtgcaca ccaagaagtg     600
aatctcgaac cgcatgttca ggaaatagaa gtgtctaggc tgttcttgga gcccacacga     660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca aggaagccca gctccctgtg     840
attgagaata agtgtgcaa tcgctatgag tttctgaatg gaagagtcca atccaccgaa      900
ctctgtgctg gcatttggc cggaggcact gacagttgcc agggtgacag tggaggtcct      960
ctggtttgct tcgagaagga caaatacatt ttacaaggag tcacttcttg gggtcttggc    1020
tgtgcacgcc ccaataagcc tggtgtctat gttcgtgttt caaggtttgt tacttggatt    1080
gagggagtga tgagaaataa ttaa                                             1104
```

<210> SEQ ID NO 10
<211> LENGTH: 367
<212> TYPE: PRT
<213> ORGANISM: Artificial sequence
<220> FEATURE:
<223> OTHER INFORMATION: amino acid sequence of
    Mini-plg(mini-plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
                20                  25                  30

Pro Ser Glu Glu Asp Cys Met Phe Gly Asn Gly Lys Gly Tyr Arg Gly
            35                  40                  45

Lys Arg Ala Thr Thr Val Thr Gly Thr Pro Cys Gln Asp Trp Ala Ala
        50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
    130                 135                 140

His Pro His Ser Trp Pro Trp Gln Val Ser Leu Arg Thr Arg Phe Gly
```

```
            145                 150                 155                 160
Met His Phe Cys Gly Gly Thr Leu Ile Ser Pro Glu Trp Val Leu Thr
                    165                 170                 175

Ala Ala His Cys Leu Glu Lys Ser Pro Arg Pro Ser Ser Tyr Lys Val
                    180                 185                 190

Ile Leu Gly Ala His Gln Glu Val Asn Leu Glu Pro His Val Gln Glu
                    195                 200                 205

Ile Glu Val Ser Arg Leu Phe Leu Glu Pro Thr Arg Lys Asp Ile Ala
        210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
        355                 360                 365

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for
      Micro-plg(micro-plasminogen)

<400> SEQUENCE: 11
gccccttcat tgattgtgg gaagcctcaa gtggagccga agaaatgtcc tggaagggtt      60 gtagggggt gtgtggccca cccacattcc tggccctggc aagtcagtct tagaacaagg     120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacatttac aaggagtcac ttcttggggt    660
cttggctgtg cacgccccaa taagcctggt gtctatgttc gtgtttcaag gtttgttact    720
tggattgagg gagtgatgag aaataattaa                                     750
```

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for
      Micro-plg(micro-plasminogen)

<400> SEQUENCE: 12

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13

| gttgtagggg ggtgtgtggc ccacccacat tcctggccct ggcaagtcag tcttagaaca | 60 |
| aggtttggaa tgcacttctg tggaggcacc ttgatatccc cagagtgggt gttgactgct | 120 |
| gcccactgct tggagaagtc cccaaggcct tcatcctaca aggtcatcct gggtgcacac | 180 |
| caagaagtga atctcgaacc gcatgttcag gaaatagaag tgtctaggct gttcttggag | 240 |
| cccacacgaa aagatattgc cttgctaaag ctaagcagtc ctgccgtcat cactgacaaa | 300 |

```
gtaatcccag cttgtctgcc atccccaaat tatgtggtcg ctgaccggac cgaatgtttc      360
atcactggct ggggagaaac ccaaggtact tttggagctg gccttctcaa ggaagcccag      420
ctccctgtga ttgagaataa agtgtgcaat cgctatgagt ttctgaatgg aagagtccaa      480
tccaccgaac tctgtgctgg gcatttggcc ggaggcactg acagttgcca gggtgacagt      540
ggaggtcctc tggtttgctt cgagaaggac aaatacattt tacaaggagt cacttcttgg      600
ggtcttggct gtgcacgccc caataagcct ggtgtctatg ttcgtgtttc aaggtttgtt      660
acttggattg agggagtgat gaga                                            684
```

```
<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine
      protease domain

<400> SEQUENCE: 14
```

| Val | Val | Gly | Gly | Cys | Val | Ala | His | Pro | His | Ser | Trp | Pro | Trp | Gln | Val |
|---|---|---|---|---|---|---|---|---|---|---|---|---|---|---|---|
| 1 | | | | 5 | | | | | 10 | | | | | 15 | |

Ser Leu Arg Thr Arg Phe Gly Met His Phe Cys Gly Gly Thr Leu Ile
           20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225

METHOD FOR PREVENTING AND TREATING TISSUE AND ORGAN FIBROSIS

CROSS-REFERENCE TO RELATED APPLICATIONS

This Application is a national stage filing under 35 U.S.C. 371 of International Patent Application Serial No. PCT/CN2017/089058, filed Jun. 19, 2017, which claims priority of International Patent Application Serial No. PCT/CN2016/110174, filed Dec. 15, 2016. The entire contents of these applications are incorporated herein by reference in their entirety.

TECHNICAL FIELD

The present invention relates to a method for preventing and treating tissue and organ fibrosis, comprising administering an effective amount of plasminogen to a subject.

BACKGROUND ART

Fibrosis is a pathological change characterized by the activation and proliferation of fibroblasts, and increased fibrous connective tissues and decreased parenchymal cells in tissues and organs. Continuous progress can lead to structural destruction and loss of function of tissues and organs. Fibrosis of vital organs seriously affects the quality of life of patients and even endangers life. Tissue fibrosis is the leading cause of disability and death in many diseases worldwide. According to the relevant statistics of the United States, about 45% of the deaths due to various diseases in this country can be attributed to the diseases of tissue fibroplasia.

Fibrotic diseases comprise diseases affecting multiple systems, such as systemic sclerosis, multifocal fibrosis, scleroderma, and nephrogenic multisystem fibrosis, and further comprise organ- and tissue-specific diseases, such as skin, cardiac, pulmonary, hepatic, renal fibrosis, etc. Different fibrosis diseases have different etiologies, such as tissue and organ injury, infection, immune response and chronic inflammation; however, their common characteristics are excessive deposition of extracellular matrix (ECM) in tissues as well as organ and tissue remodeling[1-3].

Cardiac fibrosis occurs in the development and progression of a variety of heart diseases, such as viral myocarditis, myocardial infarction, and hypertensive heart disease. Excessive cardiac fibrosis leads to impaired cardiac function and is the main cause of heart failure in many diseases, wherein inhibition and reversal of myocardial fibrosis have become important links in the treatment of cardiovascular diseases.

Hepatic fibrosis refers to a pathological process of abnormal hyperplasia of connective tissue in the liver caused by various pathogenic factors, and excessive deposition of diffuse extracellular matrix in the liver. Hepatic fibrosis can be caused by a variety of factors, such as viral infection, inflammatory response, oxidative stress, and alcoholism. The pathological features of hepatic fibrosis are that there are large amounts of fibrous tissue hyperplasia and deposition in the portal area and hepatic lobule, but no interlobular septum has been formed. In hepatic cirrhosis, pseudolobules are formed, septa appear in the central venous area and the portal area, and the normal structure of the liver is destroyed. Further progression of hepatic fibrosis is called hepatic cirrhosis. Viral hepatitis is the main chronic liver disease in China. Hepatic tissue fibrosis in chronic viral hepatitis is associated with inflammation, necrosis, viral replication and the like in the liver, and is reversible at an early stage. Therefore, therapies such as antiviral therapy, body immune function adjustment, and protecting hepatocytes are combined with anti-fibrosis, which is an active measure to prevent hepatic fibrosis.

Pulmonary fibrosis diseases comprise idiopathic pulmonary fibrosis, sarcoidosis, allergic pneumonia, pneumoconiosis, drug-induced and radiation-induced fibrosis, and a broad spectrum of diseases with varying etiologies such as fibrogenic alveolitis associated with collagen vascular disease. The main pathological features comprise lung tissue mesenchymal cell proliferation, extracellular matrix proliferation and deposition, and remodeling of lung parenchyma. At present, anti-inflammation, anti-oxidation, anti-fibroblast proliferation, collagen deposition, lung transplantation and other measures are mainly used to treat pulmonary fibrosis.

Renal fibrosis is a pathological process in which extracellular matrix and inappropriate connective tissue accumulate in the kidney, leading to renal structural changes and impaired functions. It is also a common pathway for almost all renal diseases to progress to end-stage renal failure. The process of renal fibrosis involves inflammatory response, apoptosis of innate cells and immune cells, imbalance of a variety of regulatory factors of fibrosis, and the like; therefore, renal fibrosis can be resisted through anti-inflammation, anti-apoptosis, treatment against fibrosis factors and other ways.

Chronic lesions of tissues and organs are generally accompanied by fibrosis, for example, chronic inflammation and chronic lesions of the lung are accompanied by pulmonary fibrosis. Likewise, for hepatic fibrosis, for instance, hepatitis B, hepatitis C, alcoholic liver, fatty liver, schistosomiasis and the like are accompanied by early-stage hepatic fibrosis. Since the compensatory function of the liver is very strong, fibrotic lesions have been latent in a variety of chronic liver diseases and are generally discovered when they develop into hepatic cirrhosis. In fact, hepatic cirrhosis is a serious stage of hepatic fibrosis.

Furthermore, for instance, chronic nephritis, glomerulitis, tubulitis and the like are all accompanied by renal fibrosis; and cardiovascular, cerebrovascular, and lower extremity vascular sclerosis, narrowing, or obstruction are all accompanied by vascular fibrosis.

Skin fibrosis forms scar tissues. Scar tissues are fibrous connective tissues in the aging stage formed by the remodeling and maturation of granulation tissues. In the case of trauma, fibroblasts divide and proliferate, migrate to the damaged site, produce extracellular matrix, form scar tissue, and repair trauma.

The formation of scars is a process of progressive fibrosis of granulation tissues. As such, there are more and more reticular fibers and collagen fibers, and the reticular fibers become collagenized and the collagen fibers become thicker; meanwhile, fewer and fewer fibroblasts are left, and a small number of the remaining ones are transformed into fibrocytes; the interstitial fluid is gradually absorbed, and neutrophils, macrophages, lymphocytes and plasma cells disappear successively; and capillaries are closed, degenerated, and disappear, leaving few arterioles and venules. In this way, the granulation tissue is transformed into a scar tissue composed mainly of collagen fibers with few blood vessels, which is white and tough under the naked eyes.

Scar tenacity and inelasticity, together with scar contraction can cause organ deformation and dysfunction. Therefore, scarring around the joints and vital organs often causes joint spasm or restricted movement, for instance, lumen stenosis may be caused in the lumen organs such as the digestive tract and the urinary tract, and movement disorder may be caused near the joints. Cicatricial adhesions between organs or between organs and body cavity walls often affect their function to varying degrees. If extensive fibrosis and hyaline degeneration occur after extensive injury in the organ, organ sclerosis will occur.

Systemic sclerosis (SSc), also known as scleroderma, is a systemic autoimmune disease characterized by localized or diffuse skin thickening and fibrosis. The lesions are characterized by fibrous hyperplasia of skin and onion skin changes of blood vessels, which eventually lead to skin sclerosis and vascular ischemia. The disease is clinically characterized by localized or diffuse skin thickening and fibrosis. In addition to skin involvement, it can also affect the internal organs (heart, lungs, digestive tract and other organs).

Atherosclerosis generally leads to ischemic injuries of tissues and organs, which in turn causes fibrotic lesions in tissues and organs. Atherosclerosis is a chronic, progressive arterial disease in which the fat deposited in the arteries partially or completely blocks blood flow. Atherosclerosis occurs when the otherwise smooth and solid arterial intima becomes roughened and thickened and is blocked by fat, fibrin, calcium, and cellular debris. Atherosclerosis is the chronic inflammatory hyperplasia of arterial intima, which leads to the stenosis or occlusion of large- and medium-sized arterial lumens, and causes ischemic injuries, fibrosis and even necrosis of corresponding organs and tissues.

Atherosclerosis is closely related to diabetes mellitus, which is manifested by early onset, severe degree and poor prognosis of atherosclerosis in diabetic patients, and atherosclerosis is the main cause of death in diabetic patients. Clinically, it has been found that the pathological changes of coronary arteries in diabetic patients are substantially characterized by more affected vessels, severe coronary artery stenosis, and more diffuse and severe lesions, and that the mechanism is mostly attributed to abnormal glucose metabolism causing atherosclerosis. With further in-depth research, more results indicate that diabetes mellitus-induced atherosclerosis is not caused by a single factor, but through a variety of pathways and more complex mechanisms to induce and promote the development and progression of atherosclerosis, such as polarization of macrophages, macrophage migration inhibitory factor pathway, advanced glycation end products pathway, scavenger receptor upregulation, insulin resistance, ubiquitin proteasome system activation, and platelet-derived growth factor activation pathway.[4]

At present, a large number of people are suffering from fibrosis diseases caused by various reasons, patients often have multiple organs and tissues affected, such diseases still lack effective therapies, and the social and economic burdens are relatively heavy. The studies of the present invention found that plasminogen can ameliorate tissue and organ fibrosis, and improve tissue and organ functions, thus opening up a new field for preventing and treating tissue and organ fibrosis and its related conditions.

SUMMARY OF THE INVENTION

The present invention relates to the following items:
1. A method for preventing and/or treating collagen deposition or fibrosis of a tissue and an organ and its related conditions in a subject, comprising administering an effective amount of plasminogen to the subject, wherein the subject is susceptible to tissue and organ fibrosis, has a tendency of tissue and organ fibrosis, or suffers from other diseases accompanied by tissue and organ fibrosis.

2. The method of item 1, wherein the collagen deposition or fibrosis of a tissue and an organ comprises skin fibrosis, vascular fibrosis, cardiac fibrosis, pulmonary fibrosis, hepatic fibrosis, and renal fibrosis.

3. The method of item 1 or 2, wherein the collagen deposition or fibrosis of a tissue and an organ comprises collagen deposition or fibrosis of a tissue and an organ elicited or accompanied by injuries caused by infection, inflammation, hypersensitivity, tumors, tissue ischemia, tissue and organ congestion, chemicals, radiation or environmental pollution.

4. The method of item 3, wherein the collagen deposition or fibrosis of a tissue and an organ comprises collagen deposition or fibrosis of a tissue and an organ caused by a tissue and organ lesion due to a bacterial, viral or parasitic infection.

5. The method of item 4, wherein the collagen deposition or fibrosis of a tissue and an organ comprises pulmonary fibrosis caused by *Mycobacterium tuberculosis* infection.

6. The method of item 4, wherein the collagen deposition or fibrosis of a tissue and an organ is hepatic fibrosis caused by a hepatitis B virus, hepatitis C virus or hepatitis E virus infection.

7. The method of item 4, wherein the collagen deposition or fibrosis of a tissue and an organ is hepatic fibrosis caused by schistosomiasis infection.

8. The method of item 3, wherein the collagen deposition or fibrosis of a tissue and an organ results from an aseptic inflammation or an autoimmune response.

9. The method of item 8, wherein the collagen deposition or fibrosis of a tissue and an organ is renal fibrosis caused by chronic glomerulonephritis, pyelonephritis, nephrotic syndrome, renal insufficiency, and uremia.

9. The method of item 3, wherein the collagen deposition or fibrosis of a tissue and an organ results from a tissue and organ injury caused by cancer.

10. The method of item 9, wherein the collagen deposition or fibrosis of a tissue and an organ is pulmonary fibrosis caused by lung cancer, hepatic fibrosis caused by liver cancer, or renal fibrosis caused by kidney cancer.

11. The method of item 3, wherein the collagen deposition or fibrosis of a tissue and an organ results from a chronic ischemic tissue injury.

12. The method of item 11, wherein the collagen deposition or fibrosis of a tissue and an organ is cardiac ischemic fibrosis caused by coronary atherosclerosis and coronary heart disease.

13. The method of item 11, wherein the collagen deposition or fibrosis of a tissue and an organ is renal fibrosis caused by a chronic ischemic renal injury.

14. The method of item 3, wherein the collagen deposition or fibrosis of a tissue and an organ results from tissue and organ congestion caused by a cardiovascular disease.

15. The method of item 14, wherein the collagen deposition or fibrosis of a tissue and an organ is hepatic congestion or pulmonary congestion.

16. The method of item 3, wherein the collagen deposition or fibrosis of a tissue and an organ results from a drug.

17. The method of item 16, wherein the collagen deposition or fibrosis of a tissue and an organ is drug-induced hepatic fibrosis or renal fibrosis.

18. The method of item 3, wherein the collagen deposition or fibrosis of a tissue and an organ is pulmonary fibrosis caused by inhaled chemicals or environmental pollutants.

19. The method of item 8, wherein the collagen deposition or fibrosis of a tissue and an organ results from a systemic immune disease such as systemic lupus erythematosus, systemic sclerosis, and ankylosing spondylitis.

20. The method of item 8, wherein the tissue and organ fibrosis is idiopathic pulmonary fibrosis.

21. The method of any one of items 1 to 20, wherein the tissue and organ fibrosis-related condition comprises a condition resulting from function weakening, dysfunction or loss of function of a tissue and an organ due to a fibrotic lesion.

22. The method of item 21, wherein the tissue and organ fibrosis-related condition comprises atherosclerosis, coronary heart disease, angina pectoris, myocardial infarction, arrhythmia, cerebral ischemia, cerebral infarction, renal insufficiency, uremia, hepatic dysfunction, hepatic cirrhosis, hepatic coma, dyspnea, emphysema, pulmonary heart disease, pulmonary fibrosis, and ankylosing spondylitis.

23. The method of any one of items 1 to 22, wherein the plasminogen is administered in combination with one or more other drugs or therapeutic means.

24. The method of item 23, wherein the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-fibrosis drug, an anti-arrhythmia drug, a cardiotonic drug, a diuretic drug, an anti-tumor drug, a radiotherapeutic or chemotherapeutic drug, an inflammatory regulatory drug, an immunomodulatory drug, an antiviral drug, and an antibiotic.

25. The method of any one of items 1 to 24, wherein the plasminogen has at least 75%, 80%, 85%, 90%, 95%, 96%, 97%, 98% or 99% sequence identity with SEQ ID No. 2, 6, 8, 10 or 12, and still has the plasminogen activity.

26. The method of any one of items 1 to 25, wherein the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the plasminogen activity.

27. The method of any one of items 1 to 26, wherein the plasminogen is a protein that comprises a plasminogen active fragment and still has the plasminogen activity.

28. The method of any one of items 1 to 27, wherein the plasminogen is selected from Glu-plasminogen, Lys-plasminogen, mini-plasminogen, micro-plasminogen, delta-plasminogen or their variants that retain the plasminogen activity.

29. The method of any one of items 1 to 28, wherein the plasminogen is a natural or synthetic human plasminogen, or a variant or fragment thereof that still retains the plasminogen activity.

30. The method of any one of items 1 to 28, wherein the plasminogen is an ortholog of human plasminogen from a primate or a rodent, or a variant or fragment thereof that still retains the plasminogen activity.

31. The method of any one of items 1 to 30, wherein the amino acids of the plasminogen are as shown in SEQ ID No. 2, 6, 8, 10 or 12.

32. The method of any one of items 1 to 31, wherein the plasminogen is a natural human plasminogen.

33. The method of any one of items 1 to 32, wherein the subject is a human.

34. The method of any one of items 1 to 33, wherein the subject has a lack or deficiency of plasminogen.

35. The method of any one of items 1 to 34, wherein the lack or deficiency is congenital, secondary and/or local.

36. A plasminogen for use in the method of any one of items 1 to 35.

37. A pharmaceutical composition, comprising a pharmaceutically acceptable carrier and the plasminogen for use in the method of any one of items 1 to 35.

38. A preventive or therapeutic kit comprising: (i) the plasminogen for use in the method of any one of items 1 to 35, and (ii) a means for delivering the plasminogen to the subject.

39. The kit of item 38, wherein the means is a syringe or a vial.

40. The kit of item 38 or 39, further comprising a label or an instruction for use indicating the administration of the plasminogen to the subject to implement the method of any one of items 1 to 35.

41. An article of manufacture, comprising:
a container comprising a label; and
(i) the plasminogen for use in the method of any one of items 1 to 35 or a pharmaceutical composition comprising the plasminogen, wherein the label indicates the administration of the plasminogen or the composition to the subject to implement the method of any one of items 1 to 35.

42. The kit of any one of items 38 to 40 or the article of manufacture of item 41, further comprising one or more additional means or containers containing other drugs.

43. The kit or the article of manufacture of item 42, wherein the other drugs are selected from the group of a hypolipidemic drug, an anti-platelet drug, an antihypertensive drug, a vasodilator, a hypoglycemic drug, an anticoagulant drug, a thrombolytic drug, a hepatoprotective drug, an anti-fibrosis drug, an anti-arrhythmia drug, a cardiotonic drug, a diuretic drug, an anti-tumor drug, a radiotherapeutic or chemotherapeutic drug, an inflammatory regulatory drug, an immunomodulatory drug, an antiviral drug, and an antibiotic.

In one aspect, the present invention relates to a method for preventing and/or treating collagen deposition or fibrosis of a tissue and an organ and its related conditions in a subject, comprising administering an effective amount of plasminogen to the subject, wherein the subject is susceptible to tissue and organ fibrosis, has a tendency of tissue and organ fibrosis, or suffers from other diseases accompanied by tissue and organ fibrosis. The present invention further relates to the use of plasminogen for preventing and/or treating collagen deposition or fibrosis of a tissue and an organ and its related conditions in a subject. The present invention further relates to the use of plasminogen in the preparation of a medicament for preventing and/or treating collagen deposition or fibrosis of a tissue and an organ and its related conditions in a subject. In addition, the present invention further relates to the plasminogen for preventing and/or treating collagen deposition or fibrosis of a tissue and an organ and its related conditions in a subject. In some embodiments, the collagen deposition or fibrosis of a tissue and an organ comprises skin fibrosis, vascular fibrosis, cardiac fibrosis, pulmonary fibrosis, hepatic fibrosis, and renal fibrosis. In some other embodiments, the collagen deposition or fibrosis of a tissue and an organ comprises collagen deposition or fibrosis of a tissue and an organ elicited by or present in injuries caused by infection, inflammation, hypersensitivity, tumors, tissue ischemia, tissue and organ congestion, chemicals, radiation or environmental pollution. Specifically, the collagen deposition or fibrosis of a tissue and an organ comprises collagen deposition or fibrosis of a tissue and an organ caused by a tissue and organ lesion due to a bacterial, viral or parasitic infection, wherein the collagen deposition or fibrosis of a tissue and an organ comprises pulmonary fibrosis caused by *Mycobacterium tuberculosis* infection, hepatic fibrosis caused by a hepatitis B virus, hepatitis C virus or hepatitis E virus infection, and hepatic fibrosis caused by schistosomiasis infection. In some embodiments, the collagen deposition or fibrosis of a tissue and an organ results from an aseptic inflammation or an autoimmune response. Specifically, the collagen deposition or fibrosis of a tissue and an organ is renal fibrosis caused by chronic glomerulonephritis, pyelonephritis, nephrotic syndrome, renal insufficiency, and uremia. In some other embodiments, the collagen deposition or fibrosis of a tissue and an organ results from a tissue and organ injury caused by cancer. Specifically, the collagen deposition or fibrosis of a tissue and an organ is pulmonary fibrosis caused by lung cancer, hepatic fibrosis caused by liver cancer, or renal fibrosis caused by kidney cancer. In some other embodiments, the collagen deposition or fibrosis of a tissue and an organ results from a chronic ischemic tissue injury. Specifically, the collagen deposition or fibrosis of a tissue and an organ is cardiac ischemic fibrosis caused by coronary atherosclerosis and coronary heart disease, and/or renal fibrosis caused by a chronic ischemic renal injury. In some other embodiments, the collagen deposition or fibrosis of a tissue and an organ results from tissue and organ congestion caused by a cardiovascular disease. Specifically, the collagen deposition or fibrosis of a tissue and an organ is hepatic congestion or pulmonary congestion. In some embodiments, the collagen deposition or fibrosis of a tissue and an organ results from a drug. Specifically, the collagen deposition or fibrosis of a tissue and an organ is drug-induced hepatic fibrosis or renal fibrosis. In some embodiments, the collagen deposition or fibrosis of a tissue and an organ is pulmonary fibrosis caused by inhaled chemicals or environmental pollutants. In the above-mentioned embodiments, the collagen deposition or fibrosis of a tissue and an organ results from a systemic immune disease such as systemic lupus erythematosus, systemic sclerosis, and ankylosing spondylitis. In some embodiments, the tissue and organ fibrosis is idiopathic pulmonary fibrosis.

In the above-mentioned embodiments, the tissue and organ fibrosis-related condition comprises a condition resulting from function weakening, dysfunction or loss of function of a tissue or an organ due to a fibrotic lesion. Specifically, the tissue and organ fibrosis-related condition comprises atherosclerosis, coronary heart disease, angina pectoris, myocardial infarction, arrhythmia, cerebral ischemia, cerebral infarction, renal insufficiency, uremia, hepatic dysfunction, hepatic cirrhosis, hepatic coma, dyspnea, emphysema, pulmonary heart disease, pulmonary fibrosis, and ankylosing spondylitis.

In the above-mentioned embodiments, the plasminogen is administered in combination with one or more other drugs or therapies. Specifically, the plasminogen is administered in combination with one or more drugs selected from: a hypolipidemic drug, an anti-platelet drug, an antihypertensive drug, a vasodilator, a hypoglycemic drug, an anticoagulant drug, a thrombolytic drug, a hepatoprotective drug, an anti-fibrosis drug, an anti-arrhythmia drug, a cardiotonic drug, a diuretic drug, an anti-tumor drug, a radiotherapeutic or chemotherapeutic drug, an inflammatory regulatory drug, an immunomodulatory drug, an antiviral drug, and an antibiotic.

In the above-mentioned embodiments, the plasminogen has at least 75%, 80%, 85%, 90%, 95%, 96%, 97%, 98% or 99% sequence identity with SEQ ID No. 2, 6, 8, 10 or 12, and still has the activity of plasminogen.

In the above-mentioned embodiments, the amino acids of the plasminogen are as shown in SEQ ID No. 2, 6, 8, 10 or 12. In some embodiments, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the activity of plasminogen.

In the above-mentioned embodiments, the plasminogen is a protein that comprises a plasminogen active fragment and still has the activity of plasminogen. Specifically, the plasminogen is selected from Glu-plasminogen, Lys-plasminogen, mini-plasminogen, micro-plasminogen, delta-plasminogen or their variants that retain the plasminogen activity.

In the above-mentioned embodiments, the plasminogen is a natural or synthetic human plasminogen, or a variant or fragment thereof that still retains the plasminogen activity. In some embodiments, the plasminogen is an ortholog of human plasminogen from a primate or a rodent, or a variant or fragment thereof that still retains the plasminogen activity. For example, the plasminogen is an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No. 2, 6, 8, 10 or 12.

In the above-mentioned embodiments, the subject is a human. In some embodiments, the subject has a lack or deficiency of plasminogen. Specifically, the lack or deficiency is congenital, secondary and/or local.

In one embodiment, the plasminogen is administered by systemic or topical route, preferably by the following routes: topical, intravenous, intramuscular, subcutaneous, inhalation, intraspinal, local injection, intraarticular injection or rectal route. In one embodiment, the topical administration is performed by direct administration to osteoporotic areas, for example through a means such as a dressing and a catheter.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances. In one aspect, the present invention relates to a pharmaceutical composition, comprising a pharmaceutically acceptable carrier and the plasminogen for use in the method of the present invention.

In another aspect, the present invention relates to a preventive or therapeutic kit comprising: (i) the plasminogen for use in the method of the present invention, and (ii) a means for delivering the plasminogen to the subject, in particular, the means is a syringe or a vial. In some embodiments, the kit further comprises a label or an instruction for use indicating the administration of the plasminogen to the subject to implement the methods of the present invention.

In another aspect, the present invention further relates to an article of manufacture comprising: a container comprising a label; and (i) the plasminogen for use in the methods of the present invention or a pharmaceutical composition comprising the plasminogen, wherein the label indicates the administration of the plasminogen or the composition to the subject to implement the methods of the present invention.

In the above-mentioned embodiments, the kit or the article of manufacture further comprises one or more additional means or containers containing other drugs. In some embodiments, the other drugs are selected from the group of: a hypolipidemic drug, an anti-platelet drug, an antihypertensive drug, a vasodilator, a hypoglycemic drug, an anticoagulant drug, a thrombolytic drug, a hepatoprotective drug, an anti-fibrosis drug, an anti-arrhythmia drug, a cardiotonic drug, a diuretic drug, an anti-tumor drug, a radiotherapeutic or chemotherapeutic drug, an inflammatory regulatory drug, an immunomodulatory drug, an antiviral drug, and an antibiotic.

Definition

"Fibrosis" is a lesion characterized by the activation and proliferation of fibroblasts, and increased fibrous connective tissue and decreased parenchymal cells in tissues and organs, and structural destruction and loss of function of tissues and organs, after the tissues and organs such as lung, liver, kidney, blood vessel, peritoneum, pancreas and skin are continuously injured due to various causes such as inflammation, infection, immune response, ischemia, chemicals and radiation. The term can be used interchangeably with "fibrotic lesion". The term "fibrotic lesion" encompasses fibrotic lesions in tissues and organs, such as cardiac fibrosis, pulmonary fibrosis, hepatic fibrosis, renal fibrosis, vascular fibrosis and skin fibrosis, which are caused by various factors, and further comprises the fibrotic lesions in tissues and organs, such as cardiac fibrosis, pulmonary fibrosis, hepatic fibrosis, renal fibrosis, vascular fibrosis and skin fibrosis, which are associated with the development and progression of various diseases.

After the development of fibrotic lesions in tissues and organs, their normal structures change, and the corresponding functions are weakened or lost, and thus the resulting related conditions are called "tissue and organ fibrosis-related conditions".

"Cardiac fibrosis" refers to the fibrotic lesion occurring in the development and progression of the cardiac tissue injury caused by or present in various factors (such as inflammation, infection, immune response, ischemia, chemicals, and radiation), or of heart diseases caused by various factors. Cardiac fibrosis lesions lead to impaired cardiac function, and thus the resulting related conditions are called "cardiac fibrosis-related conditions", including but not limited to the symptoms and conditions of organ and tissue ischemia caused by impaired cardiac function, such as coronary heart disease, angina pectoris, myocardial infarction, arrhythmia, cerebral ischemia, dyspnea, and renal insufficiency.

"Hepatic fibrosis" refers to pathological changes (lesions) caused by or present in various factors (such as inflammation, infection (such as viral infection), immune response, ischemia, chemicals, radiation, oxidative stress, and alcoholism), comprising the abnormal hyperplasia of connective tissue in the liver, excessive deposition of diffuse extracellular matrix in the liver, and destruction of the normal structure of liver. Further progression of hepatic fibrosis is hepatic cirrhosis, and is also encompassed within the scope of the term "hepatic fibrosis" of the present invention. Hepatic fibrosis lesions lead to impaired hepatic function, and thus the resulting related conditions are called "hepatic fibrosis-related conditions".

"Pulmonary fibrosis" refers to a pathological process caused by lung tissue mesenchymal cell proliferation, extracellular matrix proliferation and deposition, and lung parenchymal remodeling which are caused by or present in various factors (such as inflammation, infection, immune response, ischemia, chemicals, and radiation). Pulmonary fibrosis lesions lead to impaired pulmonary function, and thus the resulting related conditions are called "pulmonary fibrosis-related conditions".

"Renal fibrosis" refers to a pathological process in which abnormal accumulation of connective tissues in the kidney caused by or present in various factors (such as inflammation, infection, immune response, ischemia, chemicals, and radiation) occurs, leading to renal structural changes and impaired functions. The renal fibrosis lesion is a common pathway by which almost all renal diseases progress to the later stages.

Renal fibrosis lesions lead to impaired renal function, and thus the resulting related conditions are called "renal fibrosis-related conditions", for instance, renal insufficiency, renal failure, uremia, etc.

Chronic lesions of tissues and organs are generally accompanied by fibrosis, for example, chronic inflammation and chronic lesions of the lung are accompanied by pulmonary fibrosis. Likewise, for hepatic fibrosis, for example, hepatitis B, hepatitis C, alcoholic liver, fatty liver, schistosomiasis and the like are accompanied by early-stage hepatic fibrosis. Furthermore, for instance, chronic nephritis, glomerulitis, tubulitis and the like are all accompanied by renal fibrosis; and cardiovascular, cerebrovascular, and lower extremity vascular sclerosis, narrowing, or obstruction are all accompanied by vascular fibrosis. In the present invention, the term "fibrosis" or "fibrotic lesion" encompasses fibrotic lesions generally present in chronic lesions of various tissues and organs of the body.

"Systemic sclerosis", also known as "scleroderma", is a systemic autoimmune disease characterized by localized or diffuse skin thickening and fibrosis. The lesions are characterized by fibrous hyperplasia of skin and onion skin changes of blood vessels, which eventually lead to skin sclerosis and vascular ischemia. The disease is clinically characterized by localized or diffuse skin thickening and fibrosis. In addition to skin involvement, it can also affect the internal organs (heart, lungs, digestive tract and other organs).

"Atherosclerosis" is a chronic, progressive arterial disease in which the fat deposited in the arteries partially or completely blocks blood flow. Atherosclerosis is a progressive process. When the concentration of lipids in the blood is greatly increased, fatty streaks form along the arterial wall. These streaks can lead to deposits of fat and cholesterol, which attach to the otherwise smooth arterial intima and thus form nodules. Underneath these nodules, fibrotic scar tissue develops, leading to calcium deposition. The calcium deposits gradually develop into a chalky hard film (referred to as atherosclerotic plaque) that cannot be removed. When an artery connected to a tissue or an organ in the body is blocked, the ischemic injury to the tissue or organ caused by the blocked artery in the tissue or organ may lead to a fibrotic lesion of the tissue or organ, such as fibrosis of the heart, lung, liver, kidney, blood vessel, peritoneum, pancreas and skin.

Diabetes mellitus generally occurs with the development of atherosclerosis, and the mechanism is mostly attributed to atherosclerosis caused by abnormal glucose metabolism. With further in-depth research, more results indicate that diabetes mellitus-induced atherosclerosis is not caused by a single factor, but through a variety of ways and a more complex mechanism to induce and promote the development and progression of atherosclerosis[4]. Diabetes mellitus and its concomitant atherosclerosis may lead to tissue and organ injuries and fibrosis, such as fibrosis of the heart, lung, liver, kidney, blood vessel, peritoneum, pancreas, skin, and other tissues and organs.

DETAILED DESCRIPTION OF EMBODIMENTS

Plasmin is a key component of the plasminogen activation system (PA system). It is a broad-spectrum protease that can hydrolyze several components of the extracellular matrix (ECM), including fibrin, gelatin, fibronectin, laminin, and proteoglycan[5]. In addition, plasmin can activate some pro-matrix metalloproteinases (pro-MMPs) to form active matrix metalloproteinases (MMPs). Therefore, plasmin is considered to be an important upstream regulator of extracellular proteolysis[6,7]. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. The activity of PAs is simultaneously inhibited by the plasminogen activator inhibitor-1 (PAI-1) of uPA and tPA and regulated by the plasminogen activator inhibitor-2 (PAI-2) that primarily inhibits uPA. There are uPA-specific cell surface receptors (uPARs) that have direct hydrolytic activity on certain cell surfaces[8,9].

Plasminogen is a single-stranded glycoprotein composed of 791 amino acids and has a molecular weight of about 92 kDa[10,11]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids[12,13]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease[14]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered plasminogen is a 38 kDa fragment, comprising kringles 1-4, is a potent inhibitor of angiogenesis. This fragment is named as angiostatin and can be produced by proteolysis of plasminogen by several proteases.

The main substrate of plasmin is fibrin, and the dissolution of fibrin is the key to prevent pathological thrombosis[15]. Plasmin also has substrate specificity for several components of ECM, including laminin, fibronectin, proteoglycan and gelatin, indicating that plasmin also plays an important role in ECM remodeling[11,16,17]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis[18]. In addition, plasmin has the ability to activate certain potential forms of growth factors[19-21]. In vitro, plasmin can also hydrolyze components of the complement system and release chemotactic complement fragments.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No. 4) of the natural human plasminogen containing a signal peptide, is a glycoprotein composed of 810 amino acids, which has a molecular weight of about 90 kD and is synthesized mainly in the liver and capable of circulating in the blood; and the cDNA sequence encoding this amino acid sequence is as shown in SEQ ID No. 3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain[22,23]. The amino acid sequence (SEQ ID No. 8) of δ-plasminogen has been reported in the literature[23], and the cDNA sequence encoding this amino acid sequence is as shown in SEQ ID No. 7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid)[24]; the amino acid sequence is as shown in SEQ ID No. 10; and the cDNA sequence encoding this amino acid sequence is as shown in SEQ ID No. 9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid)[25], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "profibrinolysin" and "fibrinoclase zymogen", and the terms have the same meaning.

In the present application, the meaning of "lack" in plasminogen is that the content or activity of plasminogen in the body of a subject is lower than that of a normal person, which is low enough to affect the normal physiological function of the subject; and the meaning of "deficiency" in plasminogen is that the content or activity of plasminogen in the body of a subject is significantly lower than that of a normal person, or even the activity or expression is extremely small, and only through exogenous supply can the normal physiological function be maintained.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No.14, or an amino acid sequence having an amino acid sequence identity of at least 80%, 90%, 95%, 96%, 97%, 98% or 99% with SEQ ID No.14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowry method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2. In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction X/Y×100 wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) can also be used to express and generate the anti-Tau antibody of the present invention (e.g., a polynucleotide encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEEN™, PLURONICS™ or polyethylene glycol (PEG). Preferred lyophilized anti-VEGF antibody formulations are described in WO 97/04801, which is incorporated herein by reference.

The formulations of the invention may also comprise one or more active compounds required for the particular condition to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and □ ethyl-L-glutamic acid (Sidman et al. Biopolymers 22:547(1983)), nondegradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(-)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulfhydryl residues, lyophilizing from acidic solutions, controlling moisture content, using appropriate additives, and developing specific polymer matrix compositions.

Administration and Dosage

The pharmaceutical composition of the present invention is administered in different ways, for example by intravenous, intraperitoneal, subcutaneous, intracranial, intrathecal, intraarterial (e.g., via carotid), and intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely.

Articles of Manufacture or Kits

One embodiment of the present invention relates to an article of manufacture or a kit comprising plasminogen of the present invention or plasmin useful in the treatment of angiocardiopathy and its related conditions caused by diabetes mellitus. The article preferably includes a container, label or package insert. Suitable containers include bottles, vials, syringes and the like. The container can be made of various materials, such as glass or plastic. The container contains a composition that is effective to treat the disease or condition of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the angiocardiopathy and its related conditions caused by diabetes mellitus according to the present invention. The article may further comprise a second container containing a pharmaceutically acceptable buffer, such as phosphate buffered saline, Ringer's solution and glucose solution.

It may further comprise other substances required from a commercial and user perspective, including other buffers, diluents, filters, needles and syringes. In addition, the article comprises a package insert with instructions for use, including, for example, instructions to direct a user of the composition to administer to a patient the plasminogen composition and other drugs for treating an accompanying disease.

EXAMPLES

Example 1. Plasminogen Lowers Cardiac Fibrosis in Systemic Sclerosis Mice

Ten 12-week-old male C57 mice were randomly divided into two groups, 5 mice in each of the control group administered with vehicle PBS and the group administered with plasminogen. The mice were weighed and grouped on the day when the experiment began, i.e., Day 0. Model establishment and administration began from Day 1, wherein mice were injected with bleomycin subcutaneously at a dose of 0.1 mg/0.1 mL/mouse/day to induce systemic sclerosis[26], and plasminogen or PBS was administered for 21 consecutive days. Mice in the group administered with plasminogen were injected with plasminogen at a dose of 1 mg/0.1 mL/mouse/day via the tail vein, and an equal volume of PBS was administered to mice in the control group administered with vehicle PBS via the tail vein. The mice were sacrificed on Day 22. The hearts were fixed in 4% paraformaldehyde fixative for 24 hours. The fixed hearts were paraffin-embedded after dehydration with alcohol gradient and permeabilization with xylene. The tissue sections was 3 µm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 1:
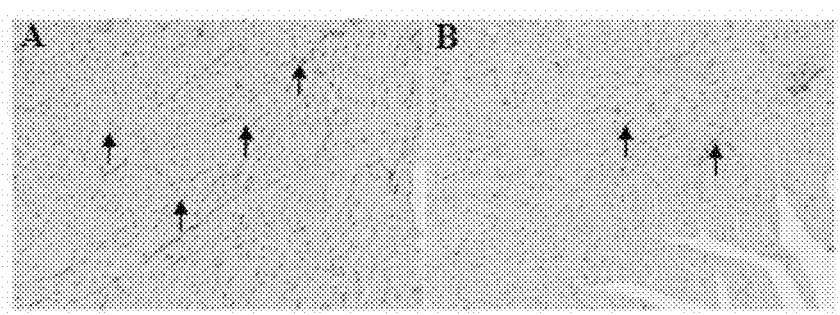
FIG. 1 shows a representative image of Sirius red staining of heart after administration of plasminogen to bleomycin-induced systemic sclerosis model mice for 21 days. A represents the control group administered with vehicle PBS, and B represents the group administered with plasminogen. Studies have found that in the bleomycin-induced systemic sclerosis mouse model, the degree of collagen deposition (indicated by arrow) in heart in the control group administered with vehicle PBS was higher than that in the group administered with plasminogen. It indicates that plasminogen can effectively reduce bleomycin-induced cardiac fibrosis.

Studies have found that in the bleomycin-induced systemic sclerosis mouse model, it was observed under a microscope that the collagen deposition in heart in the control group administered with vehicle PBS (FIG. 1A) was higher than that in the group administered with plasminogen (FIG. 1B). It indicates that plasminogen can effectively reduce bleomycin-induced cardiac fibrosis.

Example 2. Plasminogen Ameliorates Cardiac Fibrosis in 24- to 25-Week-Old Diabetic Mice Ten 24- to 25-week-old male db/db mice were randomly divided into two groups, five mice in each of a control group administered with vehicle PBS and a group administered with plasminogen. The mice were weighed and grouped on the day when the experiment began, i.e. Day 0. Plasminogen or PBS was administered from day 1 for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 31 days. The heart tissues were fixed in 4% paraformaldehyde fixative for 24 hours. The fixed heart tissues were paraffin-embedded after dehydration with alcohol gradient and permeabilization with xylene. The thickness of the tissue sections was 4 µm. The sections were dewaxed and rehydrated and then put into a potassium dichromate solution overnight. The sections were stained with iron hematocylin for 3 to 5 minutes, and flushed slightly with running water. The sections were differentiated with 1% hydrochloric acid in alcohol, treated with ammonia water for 1 second, and rinsed with water. The sections were stained in ponceau acid fuchsin fluid for 8 minutes, and rinsed rapidly in water. The sections were treated with 1% phosphomolybdic acid aqueous solution for about 2 minutes, and counterstained with aniline blue solution for 6 minutes. The sections were rinsed with 1% glacial acetic acid for about 1 minute. The sections were sealed after dehydration with absolute ethanol, and permeabilization with xylene, and were observed under an optical microscope at 200×.

The most common complication of diabetes mellitus is excessive accumulation of connective tissues (pathological fibrosis). Myocardial interstitial fibrosis may be the characteristic pathological change of diabetic cardiomyopathy[28-29].

Figure 2:
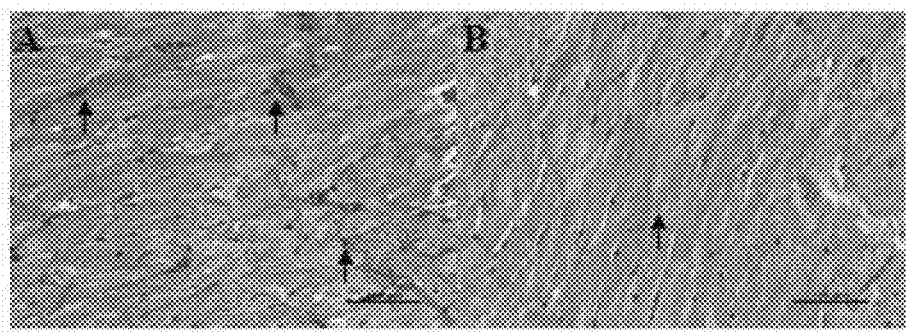
FIG. 2 shows observed results of masson staining of heart after administration of plasminogen to 24- to 25-week-old diabetic mice for 31 days. A represents the control group administered with vehicle PBS, and B represents the group administered with plasminogen. The results showed that in the control group administered with vehicle PBS, blue hyperplastic collagen fibers (indicated by arrow) could be seen between myocardial fibers, showing mild myocardial fibrosis; while in the group administered with plasminogen, a few light blue hyperplastic collagen fibers could be seen between myocardial fibers, and the myocardial fibrosis was remarkably alleviated compared with the control group. It indicates that plasminogen can ameliorate cardiac fibrosis in diabetic mice.

Masson staining can reveal tissue fibrosis. The results showed that in the control group administered with vehicle PBS (FIG. 2A), blue hyperplastic collagen fibers (indicated by arrow) could be seen between myocardial fibers, showing mild myocardial fibrosis; while in the group administered with plasminogen (FIG. 2B), a few light blue hyperplastic collagen fibers could be seen between myocardial fibers, and the myocardial fibrosis was remarkably alleviated compared with the control group. It indicates that plasminogen can ameliorate cardiac fibrosis in diabetic mice.

Example 3. Plasminogen Lowers Collagen Deposition in Heart of 17- to 18-Week-Old Diabetic Mice Eight 17- to 18-week-old male db/db micewere randomly divided into two groups, four mice in each of the control group administered with vehicle PBS and the group administered with plasminogen. The mice were weighed and grouped on the day when the experiment began, i.e. Day 0. Plasminogen or PBS was administered from day 1 for 35 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 35 days. The heart tissues were fixed in 4% paraformaldehyde fixative for 24 hours. The fixed hearts were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 3:
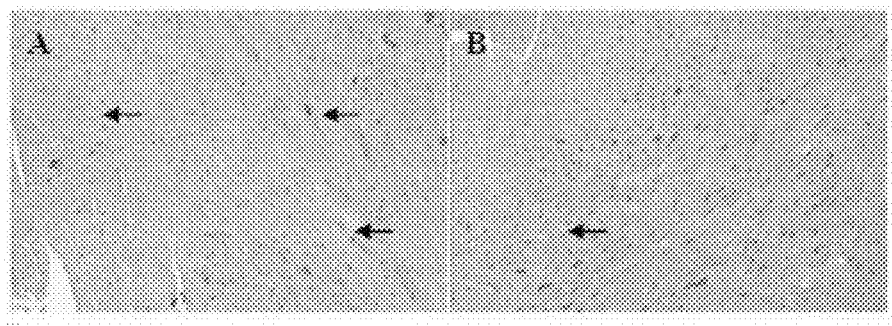
FIG. 3 shows a representative image of Sirius red staining of heart after administration of plasminogen to 17- to 18-week-old diabetic mice for 35 days. A represents the control group administered with vehicle PBS, and B represents the group administered with plasminogen. The results showed that the deposition of collagen fibers (indicated by arrow) in mice in the group administered with plasminogen was remarkably less than that in the control group administered with vehicle PBS. It indicates that plasminogen can reduce cardiac fibrosis in relatively young (17- to 18-week-old) diabetic mice.

The results showed that the deposition of collagen fibers (indicated by arrow) in mice in the group administered with plasminogen (FIG. 3B) was remarkably less than that in the control group administered with vehicle PBS (FIG. 3A). It indicates that plasminogen can reduce collagen deposition in the heart tissue, and suggests that plasminogen is expected to reduce heart tissue fibrosis in relatively young (17- to 18-week-old) diabetic mice by lowering collagen deposition in the heart tissue.

Example 4. Plasminogen Lowers Collagen Deposition in Heart of 26- to 27-Week-Old Diabetic Mice Nine 26- to 27-week-old male db/db mice were randomly divided into two groups, 5 mice in the control group administered with vehicle PBS, and 4 mice in the group administered with plasminogen. The mice were weighed and grouped on the day when the experiment began, i.e. Day 0. Plasminogen or PBS was administered from day 1 for 35 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 35 days. The heart tissues were fixed in 4% paraformaldehyde fixative for 24 hours. The fixed hearts were paraffin-embedded after dehydration with alcohol gradient and permeabilization with xylene. The tissue sections was 3 μm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Figure 4:
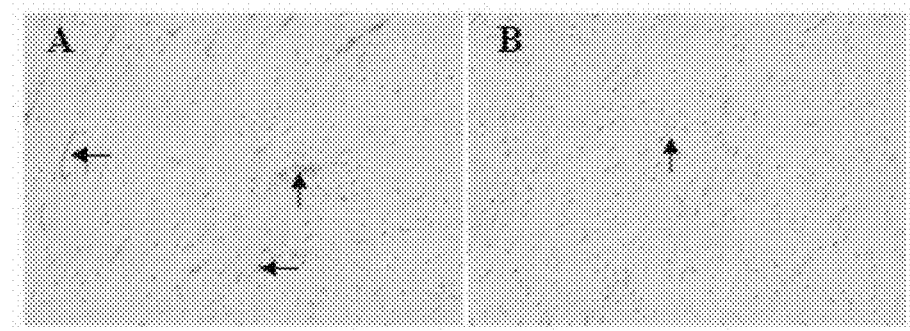
FIG. 4 shows a representative image of Sirius red staining of heart after administration of plasminogen to 26- to 27-week-old diabetic mice for 35 days. A represents the control group administered with vehicle PBS, and B represents the group administered with plasminogen. The results showed that the collagen deposition (indicated by arrow) in mice in the group administered with plasminogen was remarkably less than that in the control group administered with vehicle PBS. It indicates that plasminogen can attenuate cardiac fibrosis in relatively old (26- to 27-week-old) diabetic mice.

The results showed that the deposition of collagen fibers (indicated by arrow) in mice in the group administered with plasminogen (FIG. 4B) was remarkably less than that in the control group administered with vehicle PBS (FIG. 4A). It indicates that plasminogen can reduce collagen deposition in the heart tissue, and suggests that plasminogen is expected to reduce heart tissue fibrosis in relatively old (26- to 27-week-old) diabetic mice by lowering collagen deposition in the heart tissue.

Example 5. Plasminogen Ameliorates the Level of Cardiac Fibrosis in ApoE Atherosclerosis Mice Thirteen 6-week-old male ApoE mice were fed with a high-fat and high-cholesterol diet (Nantong TROPHIC, TP2031) for 16 weeks to induce the atherosclerosis[31,32]. 50 μL of blood was taken from each mouse three days before administration, and the total cholesterol concentration was detected. The mice were randomly divided into two groups based on the detection results, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days, during which mice continued to be fed with a high-fat and high-cholesterol diet. The mice were sacrificed on Day 31. The hearts were fixed in 4% paraformaldehyde for 24 to 48 hours. The fixed tissues were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 5:
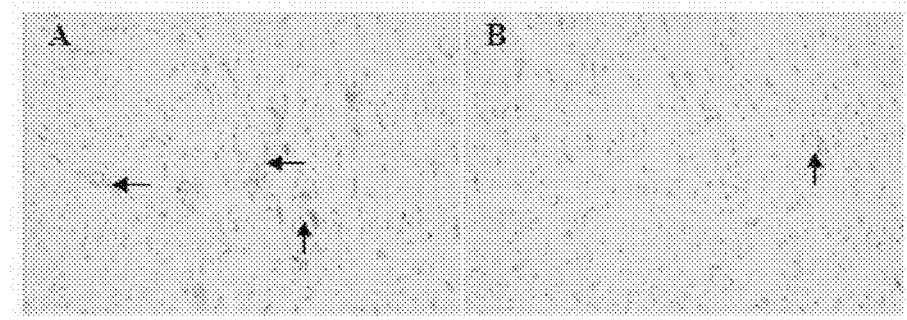
FIG. 5 shows a representative image of Sirius red staining of heart after administration of plasminogen to ApoE atherosclerosis model mice for 30 days. A represents the control group administered with vehicle PBS, and B represents the group administered with plasminogen. The results showed that the collagen deposition (indicated by arrow) in the group administered with plasminogen was remarkably less than that in the control group administered with vehicle PBS, indicating that plasminogen can alleviate cardiac fibrosis in ApoE atherosclerosis model mice.

The results showed that the collagen deposition (indicated by arrow) in the group administered with plasminogen (FIG. 5B) was remarkably less than that in the control group administered with vehicle PBS (FIG. 5A), suggesting that plasminogen can prevent and lower cardiac fibrosis induced by atherosclerosis by reducing collagen deposition in the heart tissue of ApoE atherosclerosis model mice.

Example 6. Plasminogen Lowers Cardiac Fibrosis in Hyperlipemia Model Mice

Eleven 6-week-old male C57 mice were fed with a high-fat and high-cholesterol diet (Nantong TROPHIC, TP2031) for 16 weeks to induce hyperlipemia[33,34]. 50 μL of blood was taken from each mouse three days before administration, and the total cholesterol concentration was detected. The mice were randomly divided into two groups based on the detection results, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days, during which mice continued to be fed with a high-fat and high-cholesterol diet. The mice were sacrificed on Day 31. The heart tissues were fixed in 4% paraformaldehyde for 24 to 48 hours. The fixed tissues were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 6:
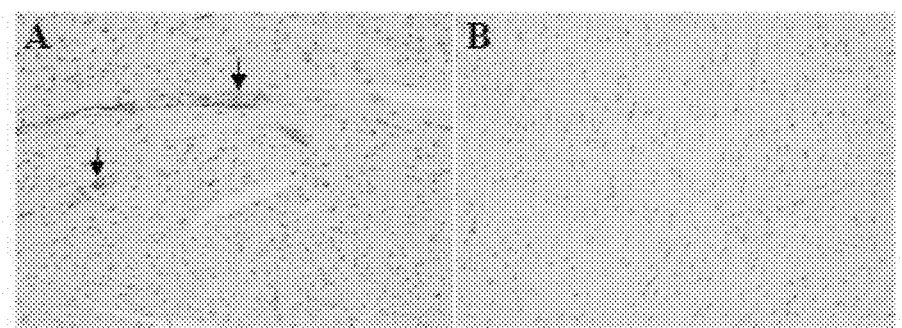
FIG. 6 shows a representative image of Sirius red staining of heart after administration of plasminogen to C57 hyperlipemia model mice for 30 days. A represents the control group administered with vehicle PBS, and B represents the group administered with plasminogen. The results showed that the collagen deposition (indicated by arrow) in the group administered with plasminogen was remarkably less than that in the control group administered with vehicle PBS, indicating that plasminogen can alleviate cardiac fibrosis in hyperlipemia model mice.

The results showed that the collagen deposition (indicated by arrow) in the group administered with plasminogen (FIG. 6B) was remarkably less than that in the control group administered with vehicle PBS (FIG. 6A), suggesting that plasminogen can prevent and lower cardiac fibrosis induced by hyperlipemia by reducing collagen deposition in the heart tissue of hyperlipemia model mice.

Example 7. Plasminogen Reduces Collagen Deposition in the Pancreatic Islet of Diabetic Mice Sixteen 24- to 25-week-old male db/db mice were randomly divided into two groups, 10 mice in the group administered with plasminogen, and 6 mice in the control group administered with vehicle PBS. Mice in the group administered with plasminogen were injected with human plasminogen at a dose of 2 mg/0.2 mL/mouse/day via the tail vein, and an equal volume of PBS was administered to mice in the control group administered with vehicle PBS via the tail vein. The mice were weighed and grouped on the day when the experiment began, i.e. Day 0. Plasminogen or PBS was administered from day 1 for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The tissue sections was 3 µm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Figure 7:
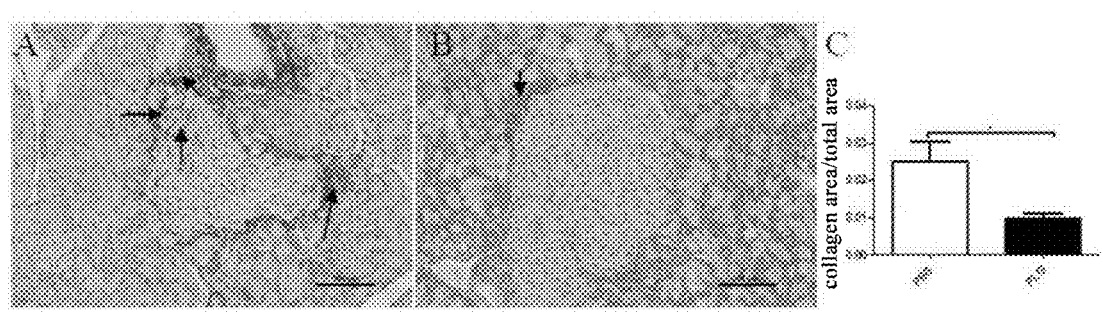
FIG. 7 shows the observed results of Sirius red-staining for pancreatic islets after administration of plasminogen to 24- to 25-week-old diabetic mice for 31 days. A represents the control group administered with vehicle PBS, B represents the group administered with plasminogen, and C represents the quantitative analysis results. The results showed that the collagen deposition (indicated by arrow) in the pancreatic islet of mice in the group administered with plasminogen was remarkably less than that in the control group administered with vehicle PBS, and the statistical difference was significant (* indicates $P<0.05$). It indicates that plasminogen can ameliorate injury and fibrosis of the pancreatic islet caused by diabetes mellitus.

The results showed that the collagen deposition (indicated by arrow) in the pancreatic islet of the mice in the group administered with plasminogen (FIG. 7B) was remarkably lower than that in the control group administered with vehicle PBS (FIG. 7A), and the statistical difference was significant (FIG. 7C). It indicates that plasminogen can significantly alleviate collagen deposition in pancreatic tissues of diabetic mice, thus preventing and alleviating pancreatic injury and fibrosis.

Figure 8:
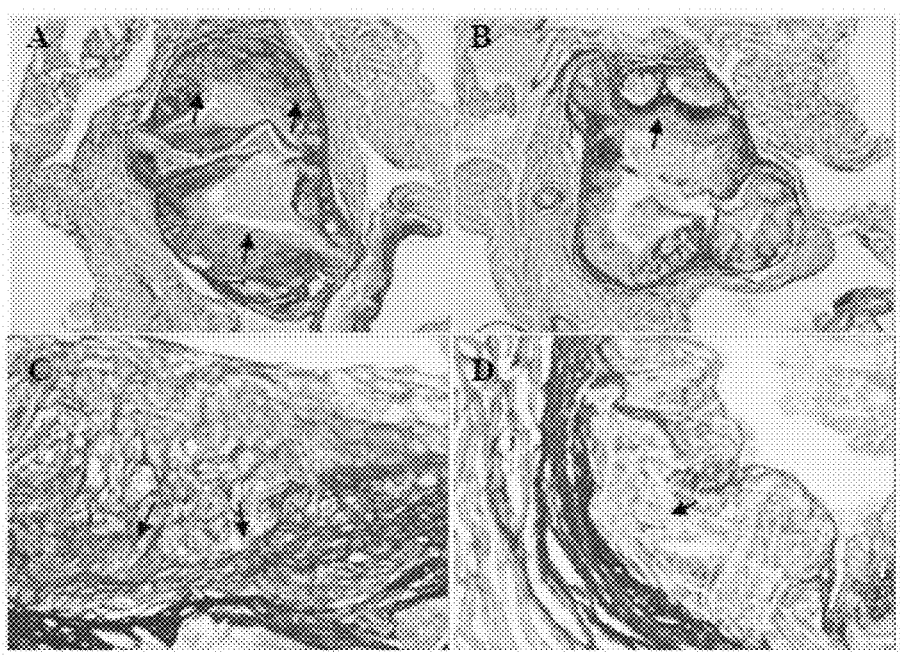
FIG. 8 shows a representative image of Sirius red staining of aortic sinus after administration of plasminogen to ApoE atherosclerosis model mice for 30 days. A and C refer to the control group administered with vehicle PBS, and B and D refer to the group administered with plasminogen. The results showed that the area of collagen deposition (indicated by arrow) in the group administered with plasminogen was remarkably less than that in the control group administered with vehicle PBS, indicating that plasminogen can reduce the level of aortic sinus fibrosis in arteriosclerosis model mice.

Example 8. Plasminogen Ameliorates Aortic Sinus Fibrosis in ApoE Atherosclerosis Mice Thirteen 6-week-old male ApoE mice were fed with a high-fat and high-cholesterol diet (Nantong TROPHIC, TP2031) for 16 weeks to induce the atherosclerosis model[31,32]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours, then sedimented in 15% and 30% sucrose at 4° C. overnight, respectively, and embedded in OCT. The frozen sections were 8 µm thick. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 40× (FIGS. 8A and 8B) and 200× (FIGS. 8C and 8D).

The results showed that the area of collagen deposition (indicated by arrow) on the intima of the aortic sinus wall in the group administered with plasminogen (FIGS. 8B and D) was remarkably less than that in the control group administered with vehicle PBS (FIGS. 8A and C), indicating that plasminogen can reduce the level of aortic sinus fibrosis in arteriosclerosis model mice.

Example 9. Plasminogen Ameliorates Carbon Tetrachloride-Induced Hepatic Fibrosis Fifteen 9-week-old female C57 mice were randomly divided into three groups, a blank control group, a control group administered with vehicle PBS, and a group administered with plasminogen, 5 mice in each group. Mice in the control group administered with vehicle PBS and the group administered with plasminogen were injected with carbon tetrachloride intraperitoneally at a dose of 1 mL/kg body weight, three times a week for two consecutive weeks, to establish the hepatic fibrosis model[36,37]; while the blank control mice were injected with a corresponding volume of corn oil according to the injection method of model mice.

Carbon tetrachloride required to be diluted with corn oil, and the dilution ratio of carbon tetrachloride to corn oil was 1:3. Administration began after model establishment. The first day of administration was recorded as Day 1. Mice in the group administered with plasminogen were injected with human plasminogen at a dose of 1 mg/0.1 mL/mouse/day via the tail vein, and mice in the control group administered with vehicle PBS were injected with an equal volume of PBS via the tail vein, both lasting for 14 consecutive days. The blank control group was not treated with injection. The mice were sacrificed on Day 15. The livers were fixed in 4% paraformaldehyde for 24 hours. The fixed livers were paraffin-embedded after dehydration with alcohol gradient and permeabilization with xylene. The tissue sections was 3 µm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Figure 9:
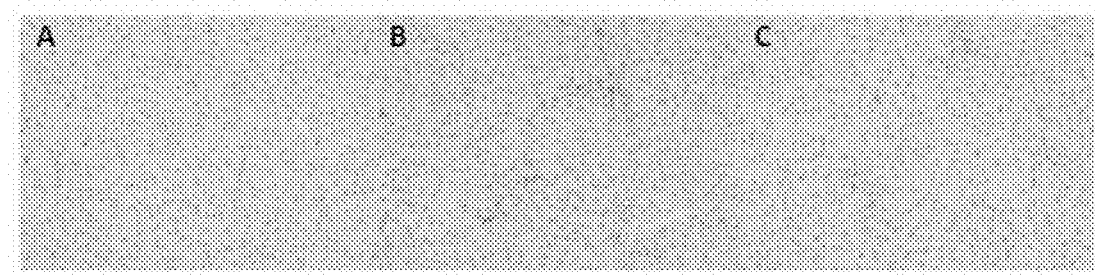
FIG. 9 shows a representative image of Sirius red staining of liver after administration of plasminogen to carbon tetrachloride-induced hepatic fibrosis model mice for 14 days. A represents a blank control group, B represents a control group administered with vehicle PBS, and C represents a group administered with plasminogen. The results showed that in the group administered with plasminogen, the collagen deposition was remarkably less than that in the control group administered with vehicle PBS, and the level of collagen deposition in mice was close to that in blank control mice. It indicates that plasminogen can reduce collagen deposition in liver, and ameliorate hepatic fibrosis in hepatic fibrosis model mice.

The results showed that the collagen deposition in the group administered with plasminogen (FIG. 9C) was remarkably less than that in the control group administered with vehicle PBS (FIG. 9B), and compared to the group administered with PBS, the level of collagen deposition in mice in the group administered with plasminogen was closer to that in blank control mice (FIG. 9A). It indicates that plasminogen can reduce collagen deposition in liver, and ameliorate hepatic fibrosis in hepatic fibrosis model mice.

Figure 10:
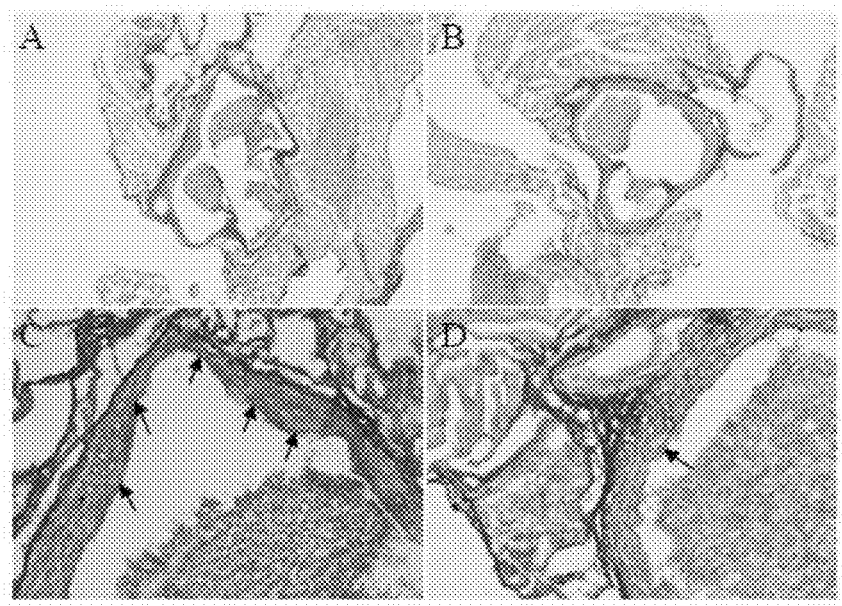
FIG. 10 shows a representative image of Sirius red staining of aortic sinus after administration of plasminogen to 16-week hyperlipemia model mice for 30 days. A and C refer to the control group administered with vehicle PBS, and B and D refer to the group administered with plasminogen. The results showed that the area of collagen deposition (indicated by arrow) on the intima of the aortic sinus wall in the group administered with plasminogen was remarkably less than that in the control group administered with vehicle PBS, indicating that plasminogen can reduce the level of intimal fibrosis of the aortic sinus wall in hyperlipemia model mice.

Example 10. Plasminogen Reduces Aortic Sinus Fibrosis in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model[30,31]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart materials were taken and fixed in 4% paraformaldehyde for 24 to 48 hours. The fixed tissues were paraffin-embedded after dehydration with alcohol gradient and permeabilization with xylene. The aortic sinus sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 40× (FIGS. 10A and 10B) and 200× (FIGS. 10C and 10D).

The results showed that the area of collagen deposition (indicated by arrow) on the intima of the aortic sinus wall in the group administered with plasminogen (FIGS. 10B and 10D) was remarkably less than that in the control group administered with vehicle PBS (FIGS. 10A and 10C), indicating that plasminogen can alleviate the level of aortic sinus fibrosis in hyperlipemia model mice.

Example 11. Plasminogen Lowers Skin Fibrosis in Systemic Sclerosis Mice

Fifteen 12-week-old male C57 mice were randomly divided into three groups, a blank control group, a control group administered with vehicle PBS (PBS refers to Phosphate Buffer Saline, as a vehicle of plasminogen herein), and a group administered with plasminogen, 5 mice in each group, and five 13-week-old mice with impaired PLG activity were taken. The mice were weighed and grouped on the day when the experiment began, i.e., Day 0. Model establishment and administration began from the next day, wherein mice in the control group administered with vehicle PBS and the group administered with plasminogen as well as mice with impaired PLG activity were injected with bleomycin subcutaneously at a dose of 0.1 mg/0.1 mL/mouse/day to induce systemic sclerosis[26]. Mice in the blank control group were injected with normal saline subcutaneously at a dose of 0.1 mL/mouse/day; meanwhile, on Day 1, plasminogen or PBS was administered for 21 consecutive days for model establishment. Mice in the group administered with plasminogen were injected with plasminogen at a dose of 1 mg/0.1 mL/mouse/day via the tail vein, an equal volume of PBS was administered to mice in the control group administered with vehicle PBS, and the normal mouse group and mice with impaired PLG activity were not treated. The mice were sacrificed on Day 22. The back skin tissues were fixed in 4% paraformaldehyde fixative for 24 hours. The fixed skin tissues were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 100×.

Sirius red staining allows for long-lasting staining of collagen. As a special staining method for pathological sections, Sirius red staining can show the collagen tissue specifically.

Figure 11:
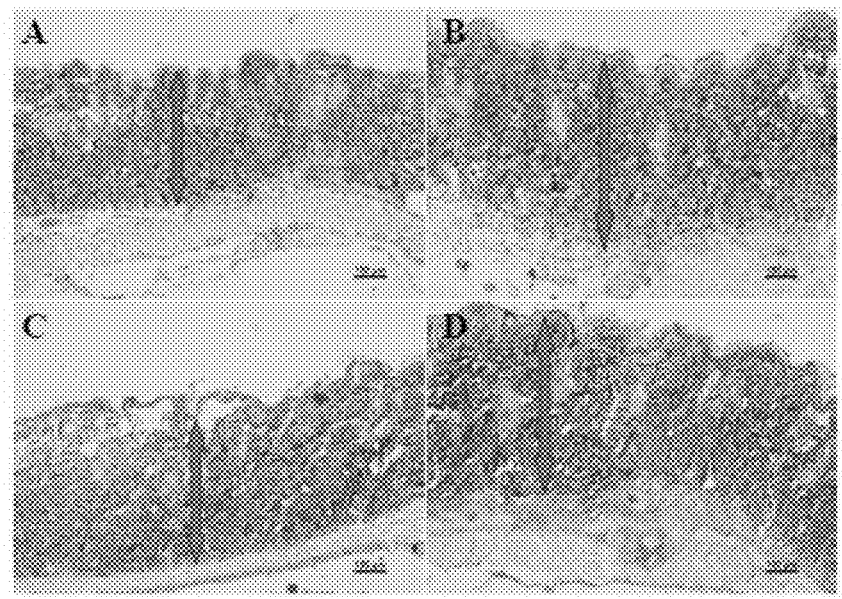
FIG. 11 shows a representative image of Sirius red staining of skin after administration of plasminogen to bleomycin-induced systemic sclerosis model mice for 21 days. A represents the blank control group, B represents the control group administered with vehicle PBS, C represents the group administered with plasminogen, and D represents the group with impaired PLG activity. The results showed that in the bleomycin-induced systemic sclerosis mouse model, the collagen fiber bundles in the upper dermis were remarkably increased, the collagen fibers were thick and big, and dense in arrangement, and the dermal layer was thickened in the group administered with vehicle PBS and the group with impaired PLG activity; while in the group administered with plasminogen, the fibroblasts in the dermal layer were remarkably less than those in the group administered with vehicle PBS, and the thickness of the dermal layer of the skin was close to the normal level.

The results showed that in the bleomycin-induced systemic sclerosis mouse model, it was observed under a microscope that the collagen fiber bundles in the upper dermis were remarkably increased, the collagen fibers were thick and big, and dense in arrangement, and the dermal layer was thickened in mice in the group administered with vehicle PBS (FIG. 11B) and the group with impaired PLG activity (FIG. 11D); while in the group administered with plasminogen (FIG. 11C), the fibroblasts in the dermal layer were remarkably less than those in the control group administered with vehicle PBS, and the thickness of the dermal layer of the skin was substantially close to the normal level (FIG. 11A). It indicates that plasminogen can effectively reduce bleomycin-induced skin fibrosis.

Example 12. Plasminogen Lowers Pulmonary Fibrosis in Systemic Sclerosis Mice

Seventeen 12-week-old male C57 mice were randomly divided into two groups, 11 mice in the control group administered with vehicle PBS, and 6 mice in the group administered with plasminogen. The mice were weighed and grouped on the day when the experiment began, i.e., Day 0. Model establishment and administration began from Day 1, wherein mice in both groups were injected with bleomycin subcutaneously at a dose of 0.1 mg/0.1 mL/mouse/day to induce systemic sclerosis[26], and plasminogen or PBS was administered for 21 consecutive days for model establishment. Mice in the group administered with plasminogen were injected with plasminogen at a dose of 1 mg/0.1 mL/mouse/day via the tail vein, and an equal volume of PBS was administered to mice in the control group administered with vehicle PBS in the same manner. The mice were sacrificed on Day 22. The lung tissues were fixed in 4% paraformaldehyde fixative for 24 hours. The fixed lung tissues were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 12:
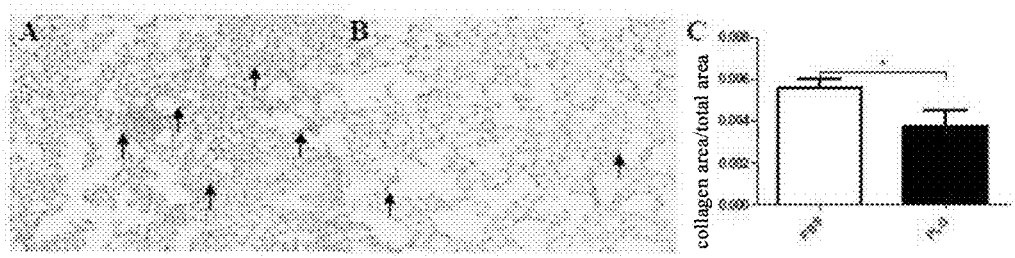
FIG. 12 shows a representative image of Sirius red staining of lung after administration of plasminogen to bleomycin-induced systemic sclerosis model mice for 21 days. A represents the control group administered with vehicle PBS, B represents the group administered with plasminogen, and C represents the quantitative analysis results. The results showed that in the bleomycin-induced systemic sclerosis mouse model, the degree of pulmonary fibrosis (indicated by arrow) in mice in the group administered with vehicle PBS was higher than that in the group administered with plasminogen; while in the group administered with plasminogen, the morphology of pulmonary alveolar walls in mice was close to normal, cells with the inflammatory level was remarkably reduced, the degree of fibrosis was remarkably lower than that in the group administered with vehicle PBS, and the statistical difference was significant (* indicates P<0.05).

Studies have found that in the bleomycin-induced systemic sclerosis mouse model, it was observed under a microscope that the degree of collagen fibrosis (indicated by arrow) in the group administered with vehicle PBS (FIG. 12A) was higher than that in the group administered with plasminogen (FIG. 12B); while in the group administered with plasminogen, the morphology of pulmonary alveolar walls in mice was close to the normal level, the inflammatory cells were remarkably reduced, the degree of fibrosis was remarkably lower than that in the group administered with vehicle PBS, and the statistical difference was significant (FIG. 12C). It indicates that plasminogen can effectively reduce lung tissue fibrosis in bleomycin-induced systemic sclerosis mice.

Example 13. Plasminogen Lowers Renal Fibrosis in Systemic Sclerosis Mice

Ten 12-week-old male C57 mice were randomly divided into two groups, 5 mice in each of the control group administered with vehicle PBS and the group administered with plasminogen. The mice were weighed and grouped on the day when the experiment began, i.e., Day 0. Model establishment and administration began from Day 1, wherein all mice were injected with bleomycin subcutaneously at a dose of 0.1 mg/0.1 mL/mouse/day to induce systemic sclerosis, and plasminogen or PBS was administered for 21 consecutive days for model establishment. Mice in the group administered with plasminogen were injected with plasminogen at a dose of 1 mg/0.1 mL/mouse/day via the tail vein, and mice in the control group administered with vehicle PBS were injected with an equal volume of PBS via the tail vein. The mice were sacrificed on Day 22. The kidneys were fixed in 4% paraformaldehyde fixative for 24 hours. The fixed kidneys were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 13:
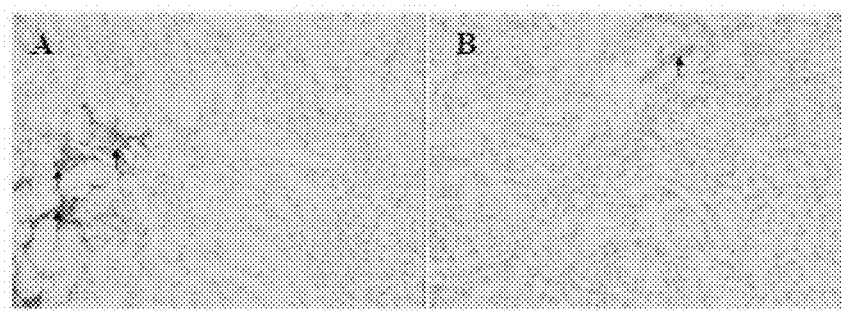
FIG. 13 shows a representative image of Sirius red staining of kidney after administration of plasminogen to bleomycin-induced systemic sclerosis model mice for 21 days. A represents the control group administered with vehicle PBS, and B represents the group administered with plasminogen. The results showed that in the bleomycin-induced systemic sclerosis mouse model, the degree of collagen fibrosis (indicated by arrow) in the kidney in the control group administered with vehicle PBS was higher than that in the group administered with plasminogen. It indicates that plasminogen can effectively reduce bleomycin-induced renal fibrosis.

The results showed that in the bleomycin-induced systemic sclerosis mouse model, the degree of collagen fibrosis (indicated by arrow) in the kidney in the control group administered with vehicle PBS (FIG. 13A) was higher than that in the group administered with plasminogen (FIG. 13B). It indicates that plasminogen can effectively reduce bleomycin-induced renal fibrosis.

Example 14. Plasminogen Lowers Collagen Deposition in Kidney of Diabetic Mice

Ten 24- to 25-week-old male db/db mice were randomly divided into two groups, five mice in each of a control group administered with vehicle PBS and a group administered with plasminogen. The mice were weighed and grouped on the day when the experiment began, i.e. Day 0. Plasminogen or PBS was administered from day 1 for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 31 days. The kidney tissues were fixed in 4% paraformaldehyde fixative for 24 hours. The fixed kidney tissues were paraffin-embedded after dehydration with alcohol gradient and permeabilization with xylene. The thickness of the tissue sections was 4 μm. The sections were dewaxed and rehydrated and washed with water once. The sections were incubated with 3% hydrogen peroxide for 15 minutes and washed with 0.01M PBS twice for 5 minutes each time. The sections were blocked with 10% normal goat serum (Vector laboratories, Inc., USA) for 1 hour, and after the time was up, the serum was thrown away, and the tissues were circled with a PAP pen. The sections were incubated with rabbit anti-mouse polyclonal antibody (Abcam) against IV collagen overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Diabetic nephropathy is a chronic complication of diabetes mellitus, and glomerular sclerosis and renal interstitial fibrosis are typical pathological changes[27].

Figure 14:
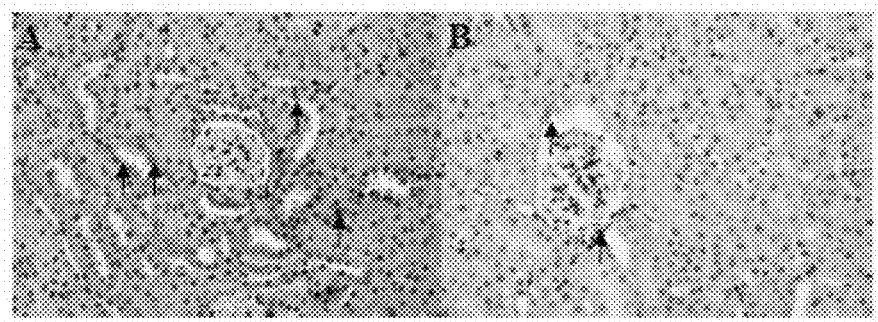
FIG. 14 shows observed results of immunostaining of type IV collagen in the kidney after administration of plasminogen to 24- to 25-week-old diabetic mice for 31 days. A represents the control group administered with vehicle PBS, and B represents the group administered with plasminogen. The results showed that the positive staining (indicated by arrow) of IV collagen in the group administered with plasminogen was remarkably higher than that in the control group administered with vehicle PBS, indicating that plasminogen can ameliorate renal fibrosis in diabetic mice.

The results showed that the positive staining of IV collagen in the group administered with plasminogen (FIG. 14B) was remarkably more than that in the control group administered with vehicle PBS (FIG. 14A), indicating that plasminogen can reduce collagen deposition (indicated by arrow) in the kidney tissue, and suggesting that plasminogen is expected to prevent renal tissue fibrosis caused by diabetes mellitus by reducing collagen deposition in the kidney tissue.

Example 15. Plasminogen Ameliorates Renal Fibrosis in Diabetic Mice

Ten 26-week-old male db/db mice were randomly divided into two groups, 5 mice in each of the control group administered with vehicle PBS and the group administered with plasminogen. The mice were weighed and grouped on the day when the experiment began, i.e. Day 0. Plasminogen or PBS was administered from day 1 for 35 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed on Day 36. The kidney tissues were fixed in 4% paraformaldehyde fixative for 24 hours. The fixed kidney tissues were paraffin-embedded after dehydration with alcohol gradient and permeabilization with xylene. The thickness of the tissue sections was 4 μm. The sections were dewaxed and rehydrated and then put into a potassium dichromate solution overnight. The sections were stained with iron hematocylin for 3 to 5 minutes, and flushed slightly with running water. The sections were differentiated with 1% hydrochloric acid in alcohol, treated with ammonia water for 1 second, and rinsed with water. The sections were stained in ponceau acid fuchsin fluid for 8 minutes, and rinsed rapidly in water. The sections were treated with 1% phosphomolybdic acid aqueous solution for about 2 minutes, and counterstained with aniline blue solution for 6 minutes. The sections were rinsed with 1% glacial acetic acid for about 1 minute. The sections were sealed after dehydration with absolute ethanol, and permeabilization with xylene, and were observed under an optical microscope at 200×.

Figure 15:
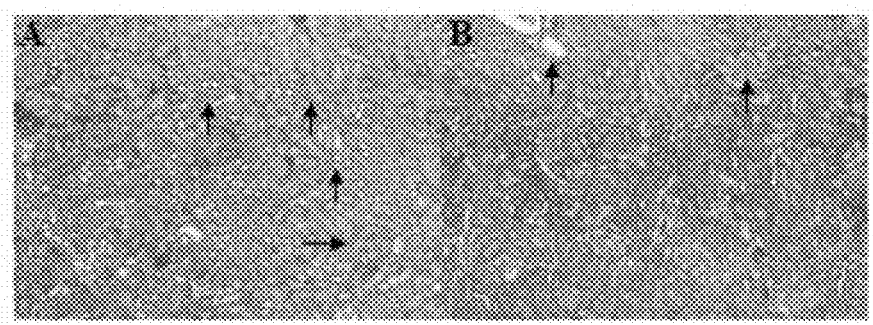
FIG. 15 shows observed results of masson staining of kidney after administration of plasminogen to 26-week-old diabetic mice for 35 days. A represents the control group administered with vehicle PBS, and B represents the group administered with plasminogen. The results showed that in the control group administered with vehicle PBS, glomerular mesangial hyperplasia existed, mesangial matrix increased, renal interstitial fibrosis was mild (indicated by arrow), and the hyperplastic fibrosis was blue. In the group administered with plasminogen, the glomerular mesangial cells and matrix were remarkably less than those in the control group, and renal interstitial fibrosis was remarkably reduced. It indicates that plasminogen can ameliorate fibrotic lesions in the kidneys of diabetic mice.

Masson staining can reveal tissue fibrosis. The results showed that in the control group administered with vehicle PBS (FIG. 15A), glomerular mesangial hyperplasia existed, mesangial matrix increased, renal interstitial fibrosis was mild (indicated by arrow), and the hyperplastic fibrosis was blue. In the group administered with plasminogen (FIG. 15B), the glomerular mesangial cells and matrix were remarkably less than those in the control group, and renal interstitial fibrosis was remarkably reduced. It indicates that plasminogen can ameliorate renal fibrosis in diabetic mice.

Example 16. Plasminogen Lowers Renal Fibrosis in Cisplatin-Induced Renal Fibrosis Model Mice Ten healthy 8-9-week-old male C57 mice were randomly divided into two groups, five mice in each of the control group administered with vehicle PBS and the group administered with plasminogen. After the completion of grouping, single intraperitoneal injection of cisplatin was performed at 10 mg/Kg body weight to establish the renal fibrosis model[30]. After the model was established, mice in the group administered with plasminogen were administered with plasminogen at a dose of 1 mg/0.1 mL/mouse/day via tail vein injection, and an equal volume of PBS was administered to mice in the control group administered with vehicle PBS. The mice were weighed and grouped on the day when the experiment began, i.e. day 0; the mice received intraperitoneal injection of cisplatin for modelling on day 1, and were administered with plasminogen or vehicle PBS 3 hours after the modelling, for an administration period of 7 days. The mice were sacrificed on Day 8. The kidneys were fixed in 4% paraformaldehyde fixative for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were repaired with citric acid for 30 minutes, and gently rinsed with water after cooling at room temperature for 10 minutes. The sections were incubated with 3% hydrogen peroxide for 15 minutes, and the tissues were circled with a PAP pen. The sections were blocked with 10% goat serum (Vector laboratories, Inc., USA) for 1 hour, and after the time was up, the goat serum liquid was discarded. The sections were incubated with rabbit anti-mouse IV collagen antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds, returned to blue with running water for 5 minutes, and washed with TBS once. After dehydration with a gradient, permeabilization and sealing, the sections were observed under an optical microscope at 200×.

Figure 16:
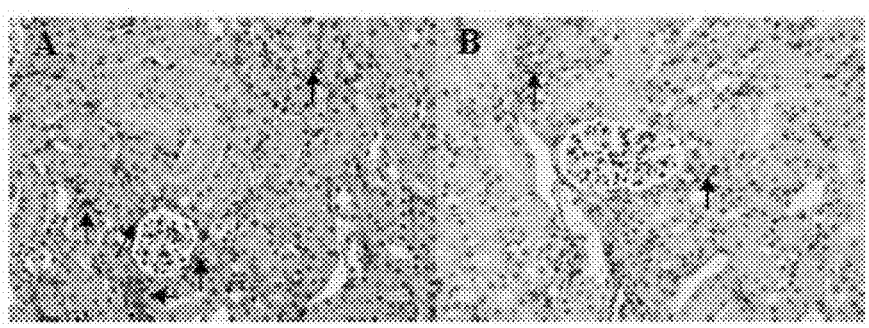
FIG. 16 shows observed results of immunostaining of type IV collagen in the kidney after administration of plasminogen to cisplatin-induced renal fibrosis model mice for 7 days. A represents the control group administered with vehicle PBS, and B represents the group administered with plasminogen. The results showed that the positive expression (indicated by arrow) of type IV collagen in the kidney in the control group administered with vehicle PBS was remarkably higher than that in the group administered with plasminogen. It indicates that plasminogen can ameliorate renal fibrosis in cisplatin-induced renal fibrosis model mice.

Cisplatin is a broad-spectrum anti-tumor drug with extensive clinical application and reliable efficacy. However, it has severe nephrotoxicity, mainly results in renal tubular and renal interstitial injuries which eventually develop into renal fibrosis[30]. The experimental results showed that the positive expression (indicated by arrow) of type IV collagen in the kidney in the control group administered with vehicle PBS (FIG. 16A) was remarkably higher than that in the group administered with plasminogen (FIG. 16B). It indicates that plasminogen can ameliorate renal fibrosis in cisplatin-induced renal fibrosis model mice.

Example 17. Plasminogen Repairs Renal Fibrosis in Chronic Renal Failure Model

Twelve 8- to 9-week-old male mice with normal PLG activity and six male mice with impaired PLG activity were taken. The mice with normal PLG activity were randomly divided into two groups, 6 mice in each of the group administered with plasminogen and the control group administered with vehicle PBS. Three groups of mice were fed with a 0.25% purine diet (Nantong TROPHIC) every day to establish the chronic renal failure model[35]. The day of model establishment was recorded as Day 1, and administration began at the same time. Mice in the group administered with plasminogen were administered with plasminogen at a dose of 1 mg/0.1 mL/mouse/day, and an equal volume of PBS was administered to mice in the control group administered with vehicle PBS in the same manner, both lasting for 10 consecutive days for model establishment. The mice with impaired PLG activity were not treated. The mice were sacrificed on Day 11. The kidneys were fixed in 4% paraformaldehyde for 24 hours. The fixed kidneys were paraffin-embedded after dehydration with alcohol gradient and permeabilization with xylene. The tissue sections was 3 µm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Figure 17:
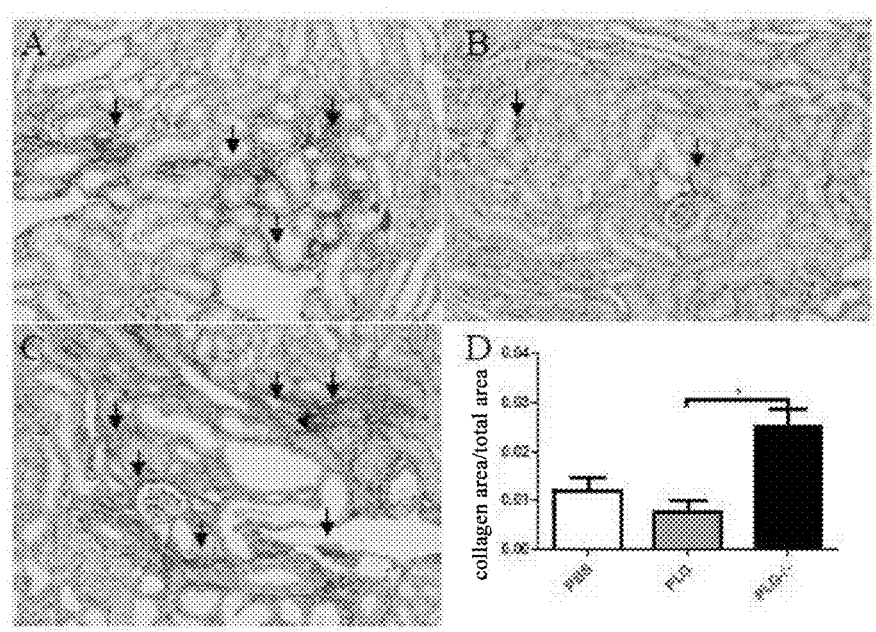
FIG. 17 shows observed results of Sirius red staining of kidney after administration of plasminogen to purine-induced chronic renal injury model mice for 10 days. A represents the control group administered with vehicle PBS, B represents the group administered with plasminogen, C represents the group with impaired PLG activity, and D represents the quantitative analysis results. The collagen deposition (indicated by arrow) in the group administered with plasminogen was remarkably less than that in the control group administered with vehicle PBS and the group with impaired PLG activity, and the quantitative analysis showed a significant statistical difference between the group administered with plasminogen and the group with impaired PLG activity (* indicates P<0.05). It indicates that plasminogen can alleviate renal fibrosis induced by chronic renal injury, and promote the repair of renal injury.

The results showed that the collagen deposition (indicated by arrow) in the group administered with plasminogen (FIG. 17B) was remarkably less than that in the control group administered with vehicle PBS (FIG. 17A) and the group with impaired PLG activity (FIG. 17C), and the statistical difference between the group administered with plasminogen and the group with impaired PLG activity was significant ($P=0.018$) (FIG. 17D). It indicates that plasminogen can significantly alleviate collagen deposition in kidney tissues of animals with chronic renal injury, thus preventing and alleviating renal fibrosis induced by chronic renal injury.

Example 18. Plasminogen Lowers Renal Fibrosis in 3% Cholesterol Hyperlipemia Model Mice Sixteen 9-week-old male C57 mice were fed with a 3% cholesterol high-fat diet (Nantong TROPHIC) for 4 weeks to induce hyperlipemia[30,31]. This model was designated as the 3% cholesterol hyperlipemia model. The model mice continued to be fed with the 3% cholesterol high-fat diet. Another five male C57 mice of the same week age were taken as the blank control group, and were fed with a normal maintenance diet during the experiment. 50 µL of blood was taken from each mouse three days before administration, and the total cholesterol was detected. The model mice were randomly divided into two groups based on the total cholesterol concentration and the body weight, i.e., the group administered with plasminogen, and the control group administered with vehicle PBS, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days. After the mice were administered on day 30, the mice were sacrificed on Day 31. The kidney materials were taken and fixed in 4% paraformaldehyde for 24 to 48 hours. The fixed tissues were paraffin-embedded after dehydration with alcohol gradient and permeabilization with xylene. The sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 18:
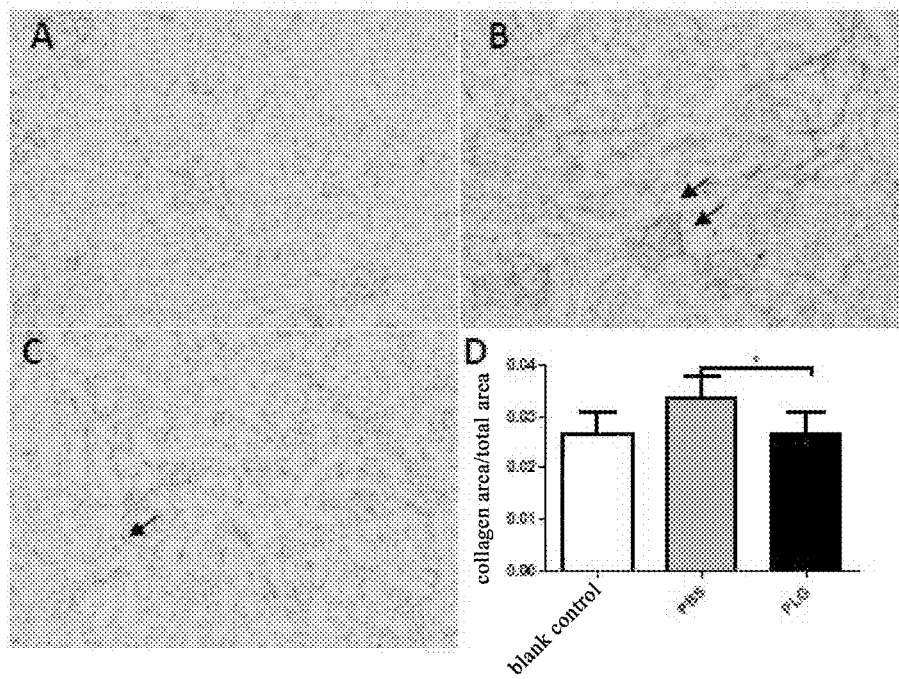
FIG. 18 shows observed results of Sirius red staining of kidney after administration of plasminogen to 3% cholesterol hyperlipemia model mice for 30 days. A represents the blank control group, B represents the control group administered with vehicle PBS, C represents the group administered with plasminogen, and D represents the quantitative analysis results. The results showed that the collagen deposition in kidney (indicated by arrow) in the group administered with plasminogen was remarkably less than that in the control group administered with vehicle PBS, and the statistical difference was significant; and in the group administered with plasminogen, fibrosis was substantially restored to a normal level. It indicates that plasminogen can effectively reduce renal fibrosis in 3% cholesterol hyperlipemia model mice.

The results showed that the collagen deposition in kidney (indicated by arrow) in the group administered with plasminogen (FIG. 18C) was remarkably less than that in the control group administered with vehicle PBS (FIG. 18B), and the statistical difference was significant (FIG. 18D); while in the group administered with plasminogen, fibrosis was substantially restored to a normal level (FIG. 18A). It indicates that plasminogen can effectively reduce renal fibrosis in 3% cholesterol hyperlipemia model mice.

Example 19. Plasminogen Reduces Collagen Deposition in Liver During Induction of Hepatic Fibrosis by Carbon Tetrachloride Twenty 7- to 8-week-old female C57 mice were randomly divided into three groups, 5 mice in the blank control group, 7 mice the control group administered with vehicle PBS, and 8 mice in the group administered with plasminogen. Mice in the control group administered with vehicle PBS and the group administered with plasminogen were injected with carbon tetrachloride intraperitoneally at a dose of 1 mL/kg body weight, three times a week for four consecutive weeks, to establish the hepatic fibrosis model[36,37]; while the blank control mice were injected with a corresponding volume of corn oil intraperitoneally. Carbon tetrachloride required to be diluted with corn oil, and the dilution ratio of carbon tetrachloride to corn oil was 1:3. Administration began on the day of model establishment, i.e., Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 28 days. The blank control group was not treated with injection. The mice were sacrificed on Day 29. The livers were fixed in 4% paraformaldehyde for 24 hours. The fixed livers were paraffin-embedded after dehydration with alcohol gradient and permeabilization with xylene. The tissue sections was 3 μm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Figure 19:
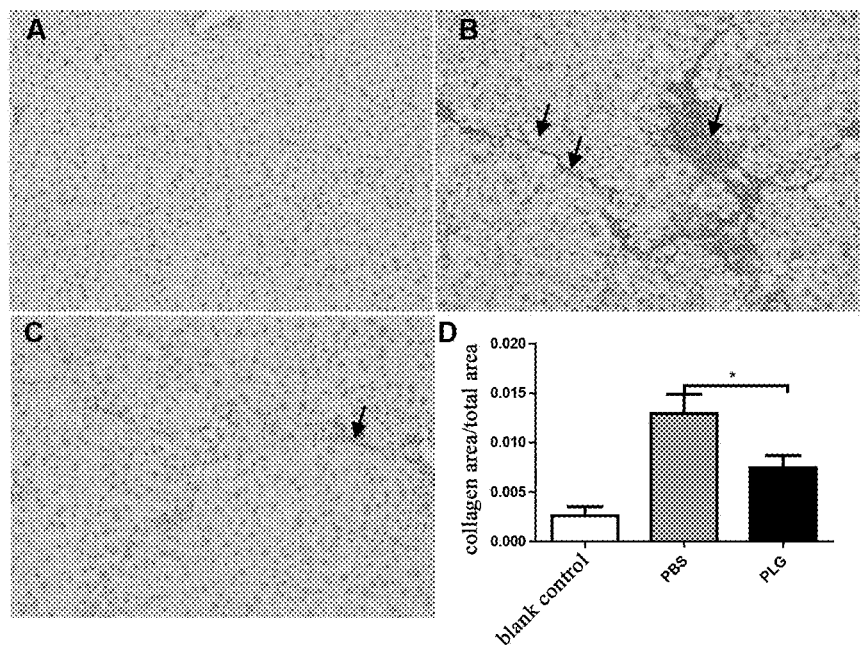
FIG. 19 shows observed results of Sirius red staining of liver after administration of plasminogen to carbon tetrachloride-induced hepatic fibrosis model mice for 28 days. A represents the blank control group, B represents the control group administered with vehicle PBS, C represents the group administered with plasminogen, and D represents the quantitative analysis results. The results showed that the collagen deposition (indicated by arrow) in the group administered with plasminogen was remarkably less than that in the control group administered with vehicle PBS, and the statistical difference was significant (* indicates P<0.05); compared with the control group administered with vehicle PBS, the level of collagen deposition in mice in the group administered with plasminogen was closer to that in blank control mice. It indicates that plasminogen can reduce collagen deposition in liver, and ameliorate hepatic fibrosis in hepatic fibrosis model mice.

The results showed that the collagen deposition in the group administered with plasminogen (FIG. 19C) was remarkably less than that in the control group administered with vehicle PBS (FIG. 19B), and the statistical difference was significant (FIG. 19D); compared with the control group administered with vehicle PBS, the level of collagen deposition (indicated by arrow) in mice in the group administered with plasminogen was closer to that in blank control mice (FIG. 19A). It indicates that plasminogen can reduce collagen deposition in liver, and ameliorate hepatic fibrosis in hepatic fibrosis model mice.

REFERENCES

[1] Denton C P, Black C M, Abraham D J. Mechanisms and consequences of fibosis in systemic sclerosis[J]. Nat Clin Pract Rheumatol, 2006, 2(3): 134-144.

[2] Wilson M S, Wynn T A. Pulmonary fibrosis: pathogenesis, etiology and regulation [J]. Mucosal Immunol, 2009, 2(2): 103-121.

[3] Liu Y. Renal fibrosis: new insights into the pathogenesis and therapeutics[J]. Kidney Int, 2006, 69: 213-217.

[4] Alexander, C. M. and Werb, Z. (1989). Proteinases and extracellular matrix remodeling. Curr. Opin. Cell Biol. 1, 974-982.

[5] Alexander C M and Werb, Z. (1991). Extracellular matrix degradation. In Cell Biology of Extracellular Matrix, Hay E D, ed. (New York: Plenum Press), pp. 255-302

[6] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.

[7] He, C. S., Wilhelm, S. M., Pentland, A. P., Marmer, B. L., Grant, G A., Eisen, A. Z., and Goldberg, G I. (1989). Tissue cooperation in a proteolytic cascade activating human interstitial collagenase. Proc. Natl. Acad. Sci. U. S. A 86, 2632-2636

[8] Stoppelli, M. P., Corti, A., Soffientini, A., Cassani, G, Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U. S. A 82, 4939-4943.

[9] Vassalli, J. D., Baccino, D., and Belin, D. (1985). A cellular binding site for the Mr 55,000 form of the human plasminogen activator, urokinase. J. Cell Biol. 100, 86-92.

[10] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[11] Saksela, O. and Rifkin, D. B. (1988). Cell-associated plasminogen activation: regulation and physiological functions. Annu. Rev. Cell Biol. 4, 93-126

[12] Raum, D., Marcus, D., Alper, C. A., Levey, R., Taylor, P. D., and Starzl, T. E. (1980). Synthesis of human plasminogen by the liver. Science 208, 1036-1037

[13] Wallén P (1980). Biochemistry of plasminogen. In Fibrinolysis, Kline D L and Reddy K K N, eds. (Florida: CRC

[14] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U. S. A 72, 2577-2581.

[15] Collen, D. and Lijnen, H. R. (1991). Basic and clinical aspects of fibrinolysis and thrombolysis. Blood 78, 3114-3124.

[16] Alexander, C. M. and Werb, Z. (1989). Proteinases and extracellular matrix remodeling. Curr. Opin. Cell Biol. 1, 974-982.

[17] Mignatti, P. and Rifkin, D. B. (1993). Biology and biochemistry of proteinases in tumor invasion. Physiol Rev. 73, 161-195.

[18] Collen, D. (2001). Ham-Wasserman lecture: role of the plasminogen system in fibrin-homeostasis and tissue remodeling. Hematology. (Am. Soc. Hematol. Educ. Program.) 1-9.

[19] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[20] Andreasen, P. A., Kjoller, L., Christensen, L., and Duffy, M. J. (1997). The urokinase-type plasminogen activator system in cancer metastasis: a review. Int. J. Cancer 72, 1-22.

[21] Rifkin, D. B., Mazzieri, R., Munger, J. S., Noguera, I., and Sung, J. (1999). Proteolytic control of growth factor availability. APMIS 107, 80-85.

[22] Marder V J, Novokhatny V. Direct fibrinolytic agents: biochemical attributes, preclinical foundation and clinical potential [J]. Journal of Thrombosis and Haemostasis, 2010, 8(3): 433-444.

[23] Hunt J A, Petteway Jr S R, Scuderi P, et al. Simplified recombinant plasmin: production and functional comparison of a novel thrombolytic molecule with plasma-derived plasmin [J]. Thromb Haemost, 2008, 100(3): 413-419.

[24] Sottrup-Jensen L, Claeys H, Zajdel M, et al. The primary structure of human plasminogen: Isolation of two lysine-binding fragments and one "mini"-plasminogen (M W, 38,000) by elastase-catalyzed-specific limited proteolysis [J]. Progress in chemical fibrinolysis and thrombolysis, 1978, 3: 191-209

[25] Nagai N, Demarsin E, Van Hoef B, et al. Recombinant human microplasmin: production and potential therapeutic properties [J]. Journal of Thrombosis and Haemostasis, 2003, 1(2): 307-313.

[26] Yosuke Kanno, En Shu, Hiroyuki Kanoh et al. The Antifibrotic Effect of a2A P Neutralization in Systemic Sclerosis Dermal Fibroblasts and Mouse Models of Systemic Sclerosis. J Invest Dermatol. 2016 April; 136(4): 762-9.

[27] Donnelly S M, Zhou X P, Huang J T et al. Prevention of early glomerulopathy with tolrestat in the streptozotocin-induced diabetic rat. Biochem Cell Biol. 1996; 74(3): 355-62.

[28] Ashish Aneja, W. H. Wilson Tang, Sameer Bansilal et al. Diabetic Cardiomyopathy: Insights into Pathogenesis, Diagnostic Challenges, and Therapeutic Options. Am J Med. 2008 September; 121(9):748-57.

[29] Samuel C S1, Hewitson T D, Zhang Y et al. Relaxin ameliorates fibrosis in experimental diabetc cardiomyopathy. Endocrinology. 2008 July; 149(7):3286-93.

[30] Yutaka Nakashima, Andrew S. Plump, Elaine W. Raines et al. Arterioscler Thromb. 1994 January; 14(1):133-40.

[31] Yutaka Nakashima, Andrew S. Plump, Elaine W. Raines et al. Arterioscler Thromb. 1994 January; 14(1):133-40.

[32] Yvonne Nitschke, Gabriele Weissen-Plenz, Robert Terkeltaub et al. Npp1 promotes atherosclerosis in ApoE knockout mice. J. Cell. Mol. Med. Vol 15, No 11, 2011 pp. 2273-2283

[33] Dominika Nackiewicz, Paromita Dey, Barbara Szczerba et al. Inhibitor of differentiation 3, a transcription factor regulates hyperlipidemia associated kidney disease. Nephron Exp Nephrol. 2014; 126(3): 141-147.

[34] Ming Gul, Yu Zhang., Shengjie Fan et al. Extracts of Rhizoma Polygonati Odorati Prevent High-Fat Diet-Induced Metabolic Disorders in C57BL/6 Mice. PLoS ONE 8(11): e81724.

[35] Cristhiane Favero Aguiar, Cristiane Naffah-de-Souza, Angela Castoldi et al. Administration of α-Galactosylceramide Improves Adenine-Induced Renal Injury. Mol Med. 2015 Jun. 18; 21:553-62.

[36] Mark A. Barnes, Megan R. McMullen, Sanjoy Roychowdhury et al. Macrophage migration inhibitory factor is required for recruitment of scar-associated macrophages during liver fibrosis. J Leukoc Biol. 2015 January; 97(1):161-9.

[37] Takayoshi Yamaza, Fatima Safira Alatas, Ratih Yuniartha et al. In vivo hepatogenic capacity and therapeutic potential of stem cells from human exfoliated deciduous teeth in liver fibrosis in mice. Stem Cell Res Ther. 2015 Sep. 10; 6:171.

The invention claimed is:

1. A method for ameliorating collagen deposition or fibrosis of a tissue and an organ in a subject having collagen deposition or fibrosis of a tissue and an organ, wherein the subject is not plasminogen-deficient, comprising administering an effective amount of plasminogen having at least 75% sequence identity to the full-length sequence of SEQ ID NOs. 2, 6, 8, 10, or 12 and comprising a plasminogen active fragment and having plasminogen activity to the subject, wherein the collagen deposition or fibrosis of a tissue and an organ comprises skin fibrosis, vascular fibrosis, cardiac fibrosis, pulmonary fibrosis, hepatic fibrosis, or renal fibrosis.

2. The method of claim 1, wherein the collagen deposition or fibrosis of a tissue and an organ comprises vascular fibrosis.

3. The method of claim 1, wherein the collagen deposition or fibrosis of a tissue and an organ comprises skin fibrosis, vascular fibrosis, cardiac fibrosis, pulmonary fibrosis, hepatic fibrosis, or renal fibrosis that is elicited by or accompanied by injuries caused by infection, inflammation, hypersensitivity, tumors, tissue ischemia, tissue and organ congestion, chemicals, radiation, or environmental pollution.

4. The method of claim 3, wherein the collagen deposition or fibrosis of a tissue and an organ comprises collagen deposition or fibrosis of a tissue and an organ caused by a tissue and organ lesion due to a bacterial infection, viral infection, or parasitic infection.

5. The method of claim 4, wherein the collagen deposition or fibrosis of a tissue and an organ comprises pulmonary fibrosis caused by *Mycobacterium tuberculosis* infection.

6. The method of claim 4, wherein the collagen deposition or fibrosis of a tissue and an organ is hepatic fibrosis caused by a hepatitis B virus infection, hepatitis C virus infection, or hepatitis E virus infection.

7. The method of claim 4, wherein the collagen deposition or fibrosis of a tissue and an organ is hepatic fibrosis caused by schistosomiasis infection.

8. The method of claim 3, wherein the skin fibrosis, vascular fibrosis, cardiac fibrosis, pulmonary fibrosis, hepatic fibrosis, or renal fibrosis results from an aseptic inflammation response.

9. The method of claim 8, wherein the renal fibrosis is caused by chronic glomerulonephritis, pyelonephritis, nephrotic syndrome, renal insufficiency, and uremia.

10. The method of claim 3, wherein the skin fibrosis, vascular fibrosis, cardiac fibrosis, pulmonary fibrosis, hepatic fibrosis, or renal fibrosis results from a chronic ischemic tissue injury.

11. The method of claim 10, wherein the cardiac fibrosis is cardiac ischemic fibrosis.

12. The method of claim 10, wherein the renal fibrosis is caused by a chronic ischemic renal injury.

13. The method of claim 3, wherein the skin fibrosis, vascular fibrosis, cardiac fibrosis, pulmonary fibrosis, hepatic fibrosis, or renal fibrosis results from tissue and organ congestion caused by a cardiovascular disease.

14. The method of claim 3, wherein the skin fibrosis, vascular fibrosis, cardiac fibrosis, pulmonary fibrosis, hepatic fibrosis, or renal fibrosis results from a drug.

15. The method of claim 14, wherein the hepatic fibrosis is drug-induced hepatic fibrosis.

16. The method of claim 8, wherein the skin fibrosis, vascular fibrosis, cardiac fibrosis, pulmonary fibrosis, hepatic fibrosis, or renal fibrosis results from a systemic immune disease.

17. The method of claim 1, wherein the pulmonary fibrosis is idiopathic pulmonary fibrosis.

18. The method of claim 1, wherein the plasminogen is administered in combination with one or more other drugs or therapeutic means.

19. The method of claim 18, wherein the one or more other drugs is selected from the group consisting of a hypolipidemic drug, an anti-platelet drug, an antihypertensive drug, a vasodilator, a hypoglycemic drug, an anticoagulant drug, a thrombolytic drug, a hepatoprotective drug, an anti-fibrosis drug, an anti-arrhythmia drug, a cardiotonic drug, a diuretic drug, an anti-tumor drug, a radiotherapeutic or chemotherapeutic drug, an inflammatory regulatory drug, an immunomodulatory drug, an antiviral drug, and an antibiotic.

20. The method of claim 1, wherein the plasminogen has at least 75%, 80%, 85%, 90%, 95%, 96%, 97%, 98% or 99% sequence identity to the full-length sequence of SEQ ID No. 2, and has the plasminogen activity.

21. The method of claim 1, wherein the plasminogen is selected from the group consisting of Glu-plasminogen, Lys-plasminogen, mini-plasminogen, micro-plasminogen, and delta-plasminogen.

22. The method of claim 1, wherein the plasminogen is a human plasminogen with SEQ ID Nos. 2, 6, 8, 10, or 12.

23. The method of claim 1, comprising administering the plasminogen to the subject at a dosage of 1-100 mg/kg.

24. The method of claim 23, wherein the administering is repeated at least once.

25. The method of claim 3, wherein the skin fibrosis, vascular fibrosis, cardiac fibrosis, pulmonary fibrosis, hepatic fibrosis, or renal fibrosis results from injuries to tissue and organs caused by cancer.

26. The method of claim 3, wherein the skin fibrosis, vascular fibrosis, cardiac fibrosis, pulmonary fibrosis, hepatic fibrosis, or renal fibrosis results from an autoimmune response.

27. The method of claim 11, wherein the cardiac ischemic fibrosis is caused by coronary atherosclerosis and coronary heart disease.

28. The method of claim 14, wherein the renal fibrosis is drug-induced renal fibrosis.

29. The method of claim 16, wherein the systemic immune disease is systemic lupus erythematosus, systemic sclerosis, or ankylosing spondylitis.

* * * * *